United States Patent
Mayo et al.

(10) Patent No.: US 11,031,117 B2
(45) Date of Patent: *Jun. 8, 2021

(54) SYSTEMS AND METHODS FOR REDUCING STRESS

(71) Applicant: VMAS Neuroscience LLC, Scottsdale, AZ (US)

(72) Inventors: Vicki Mayo, Scottsdale, AZ (US); Amy Serin, Scottsdale, AZ (US)

(73) Assignee: VMAS Solutions, Inc., Scottsdale, AZ (US)

( * ) Notice: Subject to any disclaimer, the term of this patent is extended or adjusted under 35 U.S.C. 154(b) by 214 days.

This patent is subject to a terminal disclaimer.

(21) Appl. No.: 15/438,021

(22) Filed: Feb. 21, 2017

(65) Prior Publication Data

US 2017/0296775 A1     Oct. 19, 2017

Related U.S. Application Data

(63) Continuation-in-part of application No. 15/345,916, filed on Nov. 8, 2016, now abandoned.
(Continued)

(51) Int. Cl.
*A61H 23/00*       (2006.01)
*G16H 20/70*       (2018.01)
(Continued)

(52) U.S. Cl.
CPC ............ *G16H 20/70* (2018.01); *A61M 21/02* (2013.01); *A61M 2021/0022* (2013.01)

(58) Field of Classification Search
CPC .... A61H 23/00; A61H 23/02; A61H 23/0263; A61H 2023/0272
See application file for complete search history.

(56) References Cited

U.S. PATENT DOCUMENTS 3,064,642 A * 11/1962 Stewart .............. A61H 23/0263
                                                    601/60
4,343,303 A *  8/1982 Williams ............... A61H 23/02
                                                    601/39
(Continued)

OTHER PUBLICATIONS

European Patent Office International Searching Authority, International Search Report and Written Opinion in International Application No. PCT/US2017/027046 dated Jul. 12, 2017.
(Continued)

*Primary Examiner* — Justine R Yu
*Assistant Examiner* — Christopher E Miller
(74) *Attorney, Agent, or Firm* — Transformative Legal, LLC; Len Smith; Julie Kurzrok

(57) ABSTRACT

A method for providing a therapeutic benefit to a person wearing an article having first and second tactile stimulators bilaterally positioned in the article to be in therapeutic contact with the person when the article is worn by the person. A controller (mobile device) activates the first tactile stimulator to provide a first stimulation for a first time period and activating the second tactile stimulator to apply a second stimulation for a second time period beginning at least commensurate with a cessation of the first time period. This process is repeated for a therapeutically effective number of repetitions so that the first and second stimulations are applied bilaterally to the body of the person without a perceivable pause in stimulation between the first stimulation and second stimulation to provide the therapeutic benefit to the person.

25 Claims, 29 Drawing Sheets

Related U.S. Application Data

(60) Provisional application No. 62/324,023, filed on Apr. 18, 2016.

(51) Int. Cl.
*A61M 21/02* (2006.01)
*A61M 21/00* (2006.01)

(56) References Cited

U.S. PATENT DOCUMENTS

| | | | | |
|---|---|---|---|---|
| 5,437,607 | A * | 8/1995 | Taylor | A61H 1/00 5/915 |
| 5,437,608 | A * | 8/1995 | Cutler | A61H 1/00 5/915 |
| 5,486,156 | A * | 1/1996 | Takach | A61H 23/0263 601/46 |
| 5,519,292 | A * | 5/1996 | Taylor | A61H 23/02 318/114 |
| 5,545,125 | A * | 8/1996 | Tseng | A61H 23/0263 601/70 |
| 5,575,761 | A * | 11/1996 | Hajianpour | A61H 23/0263 601/48 |
| 5,611,771 | A * | 3/1997 | Taylor | A61H 23/0263 601/48 |
| 5,836,899 | A * | 11/1998 | Reilly | A43B 3/0005 601/46 |
| 6,001,073 | A | 12/1999 | Schmidt et al. | |
| 6,039,702 | A * | 3/2000 | Cutler | A61H 23/0263 601/15 |
| 6,217,533 | B1 * | 4/2001 | McCambridge | A61H 23/0263 601/56 |
| 6,290,661 | B1 * | 9/2001 | Cutler | A61H 23/02 601/49 |
| 6,375,630 | B1 * | 4/2002 | Cutler | A61H 23/0263 601/57 |
| 6,409,655 | B1 | 6/2002 | Wilson et al. | |
| 6,422,992 | B1 * | 7/2002 | Raffel | A61M 21/00 600/27 |
| 7,152,345 | B2 * | 12/2006 | Koenig | A43B 3/0005 36/136 |
| 7,153,283 | B1 * | 12/2006 | Triolo | A61H 15/0078 601/102 |
| 7,614,168 | B1 * | 11/2009 | Zummer | A61H 15/0078 36/141 |
| 7,832,124 | B2 * | 11/2010 | Blockton | A43B 3/0005 36/136 |
| 8,142,373 | B1 * | 3/2012 | Riles | A61H 23/02 601/46 |
| 8,322,055 | B1 * | 12/2012 | Saint-Cyr | A61H 23/02 36/141 |
| 8,644,967 | B2 * | 2/2014 | Seiler | A43B 3/00 700/94 |
| 2002/0035995 | A1 | 3/2002 | Schmidt et al. | |
| 2004/0133133 | A1 * | 7/2004 | Dreimann | A61H 23/0263 601/15 |
| 2004/0260211 | A1 * | 12/2004 | Maalouf | A61H 23/02 601/15 |
| 2005/0113723 | A1 | 5/2005 | Ueyama et al. | |
| 2005/0113724 | A1 * | 5/2005 | Wriggle | A61H 23/02 601/46 |
| 2008/0027363 | A1 * | 1/2008 | Brueckmann | A61H 23/0263 601/70 |
| 2009/0005713 | A1 * | 1/2009 | Podrazhansky | A61H 23/0236 601/2 |
| 2009/0076421 | A1 * | 3/2009 | Grant, Jr. | A61H 11/00 601/47 |
| 2009/0171418 | A1 * | 7/2009 | Sarif | A61H 39/002 607/59 |
| 2009/0187124 | A1 * | 7/2009 | Ludlow | A61H 39/007 601/47 |
| 2011/0232134 | A1 * | 9/2011 | Radi | A43B 3/0005 36/141 |
| 2011/0271554 | A1 * | 11/2011 | Jazdanian | A43B 3/0005 36/43 |
| 2012/0022415 | A1 | 1/2012 | Mullen et al. | |
| 2012/0023785 | A1 * | 2/2012 | Barnes | A61F 5/14 36/141 |
| 2012/0157895 | A1 | 6/2012 | Barlow et al. | |
| 2012/0186101 | A1 * | 7/2012 | Sanchez | A43B 3/0005 36/44 |
| 2012/0197337 | A1 | 8/2012 | Su et al. | |
| 2012/0253236 | A1 * | 10/2012 | Snow | A61N 5/0618 601/2 |
| 2012/0302929 | A1 * | 11/2012 | Tkachenko | A61H 23/0254 601/48 |
| 2013/0041296 | A1 * | 2/2013 | Tass | A61H 7/001 601/15 |
| 2013/0204169 | A1 * | 8/2013 | Poepperling | A61H 9/0078 601/46 |
| 2013/0296745 | A1 * | 11/2013 | Cheatham, II | A61H 23/00 601/18 |
| 2013/0303953 | A1 * | 11/2013 | Lattner | A61M 21/00 601/47 |
| 2013/0345606 | A1 * | 12/2013 | Ehrenreich | A61H 1/00 601/46 |
| 2014/0107542 | A1 * | 4/2014 | Schubert | A61H 23/02 601/46 |
| 2014/0142477 | A1 * | 5/2014 | Park | A61H 23/02 601/46 |
| 2014/0179986 | A1 | 6/2014 | Kelley | |
| 2014/0350442 | A1 * | 11/2014 | Park | A61N 1/0484 601/48 |
| 2015/0038886 | A1 * | 2/2015 | Snow | A61H 23/0236 601/46 |
| 2015/0119770 | A1 * | 4/2015 | Driscoll | A61H 23/02 601/48 |
| 2015/0182418 | A1 * | 7/2015 | Zaiss | A61H 1/005 601/57 |
| 2015/0290074 | A1 * | 10/2015 | Koenig | A43B 3/001 601/46 |
| 2015/0305974 | A1 * | 10/2015 | Ehrenreich | A61H 23/004 601/46 |
| 2015/0328081 | A1 * | 11/2015 | Goldenberg | A61H 23/02 600/38 |
| 2015/0328082 | A1 * | 11/2015 | Jiang | A61H 19/00 600/38 |
| 2016/0001034 | A1 * | 1/2016 | Rembrand | A61H 9/0078 600/27 |
| 2016/0022533 | A1 * | 1/2016 | Makower | A61H 23/00 601/46 |
| 2016/0030279 | A1 * | 2/2016 | Driscoll | A61H 23/02 601/15 |
| 2016/0074276 | A1 * | 3/2016 | Scheuring | A61H 9/0071 600/479 |
| 2016/0242995 | A1 | 8/2016 | Karkkainen | |
| 2016/0346501 | A1 * | 12/2016 | Hooper | A61H 23/04 |
| 2017/0119619 | A1 * | 5/2017 | Dills | A61H 19/30 |
| 2017/0135896 | A1 * | 5/2017 | Snow | A61H 23/0236 |
| 2017/0274173 | A1 * | 9/2017 | Ryotokuji | A61H 39/08 |
| 2017/0340270 | A1 * | 11/2017 | Ganesh | A61B 5/0205 |
| 2017/0348184 | A1 * | 12/2017 | Pisharodi | A61F 7/007 |
| 2018/0315504 | A1 | 11/2018 | Inada et al. | |
| 2019/0029907 | A1 * | 1/2019 | Lee | A61N 5/06 |
| 2019/0070057 | A1 | 3/2019 | Conner et al. | |
| 2019/0307983 | A1 * | 10/2019 | Goldman | A61M 21/02 |

OTHER PUBLICATIONS

European Summons for EP Application 17720917.8 issued Oct. 23, 2020.

\* cited by examiner

SYSTEMS AND METHODS FOR REDUCING STRESS

RELATED APPLICATIONS

This application is a continuation-in-part of application Ser. No. 15/345,916, filed Nov. 8, 2016, which is pending. This application claims the benefit of U.S. Provisional Application No. 62/324,023 filed Apr. 18, 2016.

TECHNICAL FIELD

The technical field generally relates to stress reduction, and more particularly relates to a system and method for reducing stress to improve concentration and performance.

BACKGROUND

Stress is one of the most pervasive psychological complaints. Stress has been linked to digestive distress, headaches, depression, sleep problems, weight gain, underachievement, panic, avoidance, and poor physical health. When stress triggers the sympathetic nervous system, performance worsens. Returning an individual to a calm state as soon as possible is desirable. Once stress is experienced over time, the brain develops neural "habits" that overemphasize the stress response. When stress ensues it is known to increase body inflammation and is often impeding performance and the ability to carry out normal daily activities to one's potential.

In many adults, stress begins in childhood as a result from genetic predispositions, and/or traumatic physical or emotional distress. Stress adversely impacts brain development and creates over activation of the sympathetic nervous system, resulting in performance degradation, preoccupation, depression, anxiety, over-reactivity, and sub-optimal functioning in other areas of the brain. The brain's structure and function can be significantly altered in ways that promote ongoing stress and less adaptability. The more stress experienced in childhood has been shown to correlate with a number of negative outcomes related not only to psychological problems, but also physical disease and mortality.

Accordingly, it is desirable to provide methods and systems for disrupting the brain's habit of over-activating the sympathetic nervous system as a result of stress. It is further desirable that the systems and methods are easy to use and do not impede individuals mobility or performance of their job or other everyday tasks. It is further desirable that the systems and methods can be integrated into articles of daily life and available for use at a person's convenience. Other desirable features and characteristics will become apparent from the subsequent summary and detailed description and the appended claims, taken in conjunction with the accompanying drawings and the foregoing technical field and background.

BRIEF SUMMARY

Various non-limiting embodiments of an alternating bilateral stimulation system and method for providing a therapeutic benefit to a person are disclosed herein.

In a first non-limited embodiment, a method for providing a therapeutic benefit to an individual wearing an article having first and second tactile stimulators bilaterally positioned in the article to be in therapeutic contact with the person when the article is worn by the person. The method includes, but is not limited to, activating the first tactile stimulator to provide a first stimulation for a first time period beginning at least commensurate with a cessation of the first time period. This process is repeated for a therapeutically effective number of repetitions so that the first and second stimulations are applied bilaterally to the body of the person without the person experiencing a perceivable pause in stimulation between the first stimulation and the second stimulation, to provide the therapeutic benefit to the person.

In another non-limiting embodiment, a system for providing a therapeutic benefit to an individual includes, but is not limited to, first and second tactile stimulators bilaterally positioned in an article in therapeutic contact with a body of a person when the article is worn by the individual. The system further includes, but is not limited to, a controller communicably coupled to the first and second tactile simulators, the controller causing the first tactical stimulator to apply a first stimulation for a first time period and causing the second tactile stimulator to apply a second stimulation for a second time period beginning at least commensurate with a cessation of the first time period. So configured, the system provides a therapeutic benefit to the person by the first and second stimulations being applied bilaterally to the body of the person without the person experiencing a perceivable pause in stimulation between the first stimulation and the second stimulation, to provide the therapeutic benefit to the person.

In another non-limiting embodiment, a non-transitory computer readable medium embodying a computer program product includes, but is not limited to, instructions for providing a therapeutic benefit to a person when executed by a processor. The instructions cause the processor to communication with first and second tactile stimulators bilaterally positions on the person's body and activate and first tactile stimulator to apply a first stimulation for a first time period and activate the second tactile stimulator to apply a second stimulation for a second time period beginning at least commensurate with the processor instructing a first tactile stimulator to cease applying the first stimulation. In this way, the instructions contained in the non-transitory computer readable medium cause the first and second stimulations to apply alternating bilateral stimulation to the person without the person experiencing a perceivable pause in stimulation between the first stimulation and second stimulation, to provide the therapeutic benefit to the person.

DESCRIPTION OF THE DRAWINGS

Embodiments of the present invention will hereinafter be described in conjunction with the following drawing figures, where like numerals denote like elements, and.

DETAILED DESCRIPTION

As used herein, the word "exemplary" means "serving as an example, instance, or illustration." The following detailed description is merely exemplary in nature and is not intended to limit application and uses. Any embodiment described herein as "exemplary" is not necessarily to be construed as preferred or advantageous over other embodiments. All of the embodiments described in this Detailed Description are exemplary embodiments provided to enable persons skilled in the art to make or use the embodiment and not to limit the scope that is defined by the claims. Furthermore, there is no intention to be bound by any expressed or implied theory presented in the preceding Technical Field, Background, Drawings Summary or the following Detailed Description.

Figure 1:
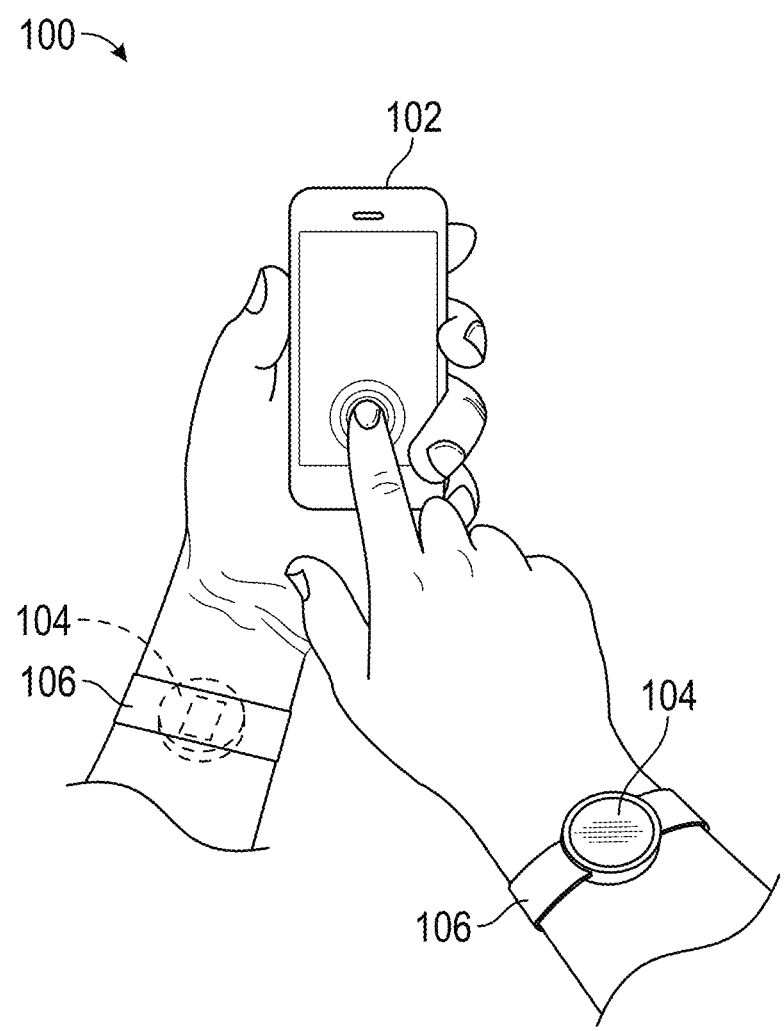
FIG. 1 is an illustration of a bilateral stimulation system in accordance with a non-limiting embodiment.

FIG. 1 is an illustration of a bilateral stimulation system 100 in accordance with a non-limiting embodiment. The stimulation system 100 is said to be bilateral, as stimulation is applied to opposing sides of individual's body. In the embodiment illustrated in FIG. 1, vibrating elements 104 are brought into therapeutic contact with the individual by being coupled to the individual's wrists by a band 106. As used herein, "therapeutic contact" means that the individual need be able to perceive the stimulation provided by the bilateral vibrating elements 104 during the therapy period. Non-limiting examples of therapeutic contact include direct contact, contact through a coupling medium (adhesive or gel), through clothing, accessories or articles being used by the individual. According to exemplary embodiments, as long as the stimulation (vibrating) elements 104 are in therapeutic contact with the individual during the therapy period, the individual will experience a therapeutic benefit from the bilateral stimulation system 100. As used herein, a "therapeutic benefit" means an actual or perceived reduction in stress or a lessening of distressing body sensations experienced by the individual using bilateral stimulation system 100.

The vibrating (stimulation) elements 104 are controlled by a mobile device 102 (e.g., cell phone, tablet computer, personal digital assistant or remote control device) running a software application (or app) that wirelessly communicates with the vibrating elements 104 via the mobile device 102 causing them to vibrate.

In one exemplary embodiment, bi-lateral asynchronous stimulation is provided by the vibrating elements 104. As used herein, "asynchronous" means to stimulate each vibrating element 104 in an alternating manner with some period of overlap where both stimulating elements are vibrating simultaneously. The overlap area may begin randomly or may be programed as will be discussed below. The vibrating elements 104 alter the brain's internal communication in multiple areas including the somatosensory cortex and other brain networks. This interferes with the brain's ability to activate the sympathetic nervous system and therefore reduces the stress response. By applying the bi-lateral and asynchronous stimulation to the individual's body, the individual experiences a reduction in stress and a lessening of distressing body sensations (e.g., racing heartbeat, stomach aches). Because the brain can activate sympathetic arousal in hundreds of milliseconds (or faster via the brain's primitive routes of processing), the overlap period provides an advantage over conventional bi-lateral stimulators in ensuring that any stimulation gap commonly used in conventional bi-lateral stimulators will not allow the brain to activate the sympathetic system. The stimulation provided during the overlap period also enhances bi-lateral impact in the somatosensory areas of the individual's brain.

In another exemplary embodiment, continuous bi-lateral stimulation is provided by the vibrating elements 104. As used herein, "continuous" means to stimulate each vibrating element 104 in an alternating manner without any perceivable gap or pause between the stimulation being applied to opposing (bi-lateral) sides of the body. Similar to asynchronous stimulation, continuous bi-lateral stimulation alters the brain's internal communication in multiple areas including the somatosensory cortex and other brain networks continuously so as not to provide time for the brain to activate the sympathetic system.

Figure 2:
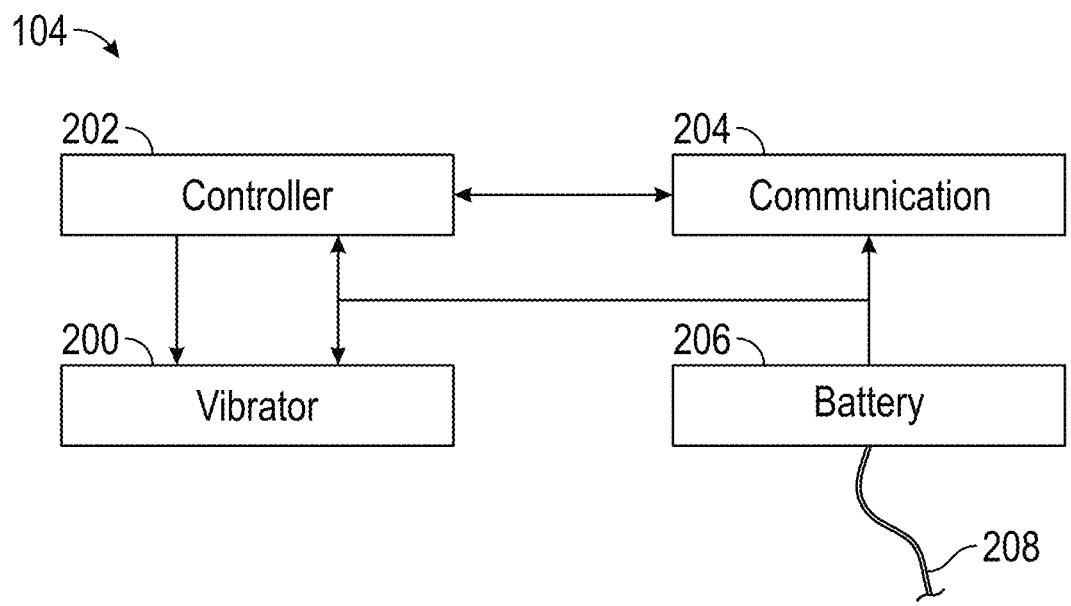
FIG. 2 is a block diagram of the stimulation elements of FIG. 1 in accordance with a non-limiting embodiment.

Referring now to FIG. 2, a block diagram of a vibrating element 104 is shown. The vibrating element includes a vibrator 200, which in some embodiments is a piezoelectric vibrator as is known in the art. The vibrator 200 is controlled by a controller 202 which receives instructions via the communication module 204 from the mobile device 102 (see FIG. 1). A battery 206 provides power to each of the components of vibrating element 104. The battery 206 may utilize any suitable battery chemistry, including, but not limited to, alkali, metal-hydride, lithium and maybe rechargeable or replaceable depending upon the implementation in any given embodiment. In some embodiments, the battery 206 may be coupled via cable 208 to power or recharge the battery 206 from a supplemental power source (not shown in FIG. 2) such as the mobile device 102 (see, FIG. 1). The cable 208 may be fitted with a micro USB connector or other suitable connector as will be appreciated by those skilled in the art. The communication module 204 may be any form of low-power wireless communication (e.g., BLUETOOTH, WIFI). In some embodiments, controller 202 comprises one or more processors. The processor(s) may reside in single integrated circuit, such as a single or multi-core microprocessor, or any number of integrated circuit devices and/or circuit boards working in cooperation to accomplish the functions of the controller 202. The processor(s) may be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The controller 202 may also contain a memory system, such as non-volatile memory (e.g., Read Only Memory (ROM), flash memory, etc.), volatile memory (e.g., Dynamic Random Access Memory (DRAM)), or some combination of the two.

Figures 3A, 3B:
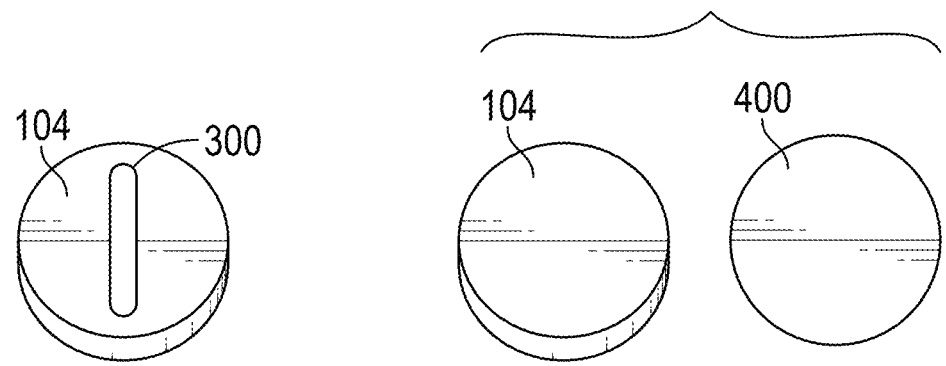
FIGS. 3A-3B are illustrations of non-limiting embodiments of the stimulation elements of FIG. 2.

FIGS. 3A and 3B are illustrations of two non-limiting embodiments of the vibrating element 104. In FIG. 3A, the vibrating element 104 is a fixed with a clip 300 that an individual can attach to a band around a portion of individuals body (e.g., wrist, arm, chest, leg) to position the vibrating element 104. In the embodiment illustrated in FIG. 3B, the vibrating element 104 may be temporarily fixed to an individual's body by a removable adhesive disc 400. In still other embodiments a hook-and-eye attachment mechanism maybe used as is known in the art.

Figure 4:
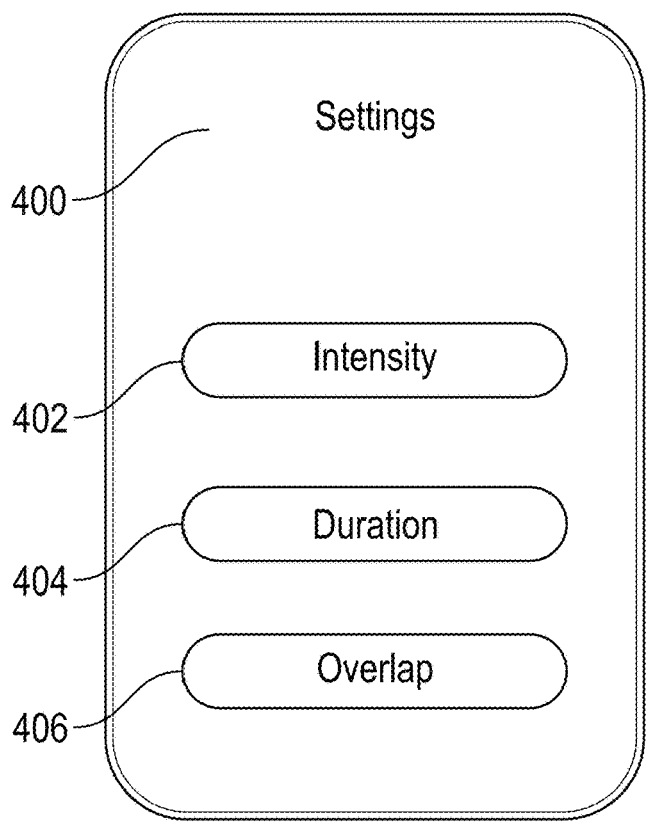
FIG. 4 is an illustration of a mobile device screen-shot for programming the stimulation applied by the stimulation elements in accordance with non-limiting embodiments.

FIGS. 4-8, are non-limiting illustrations of a display screen of the mobile device (102) that may be used to program the alternating asynchronous bilateral simulation of the bilateral stimulation system (100). In FIG. 4, a settings screen 400 is illustrated having a touch-sensitive button 402 to adjust the intensity of the vibrations, a button 404 to adjust the duration of the vibrations and a button 406 to adjust the overlap period during which both vibrating elements 104 are simultaneously applying stimulation to an individual's body. If no settings are provided (programed) by the individual, the continuous bi-lateral stimulation mode is selected, with constant intensity and speed over the stimulation time periods.

Figure 5:
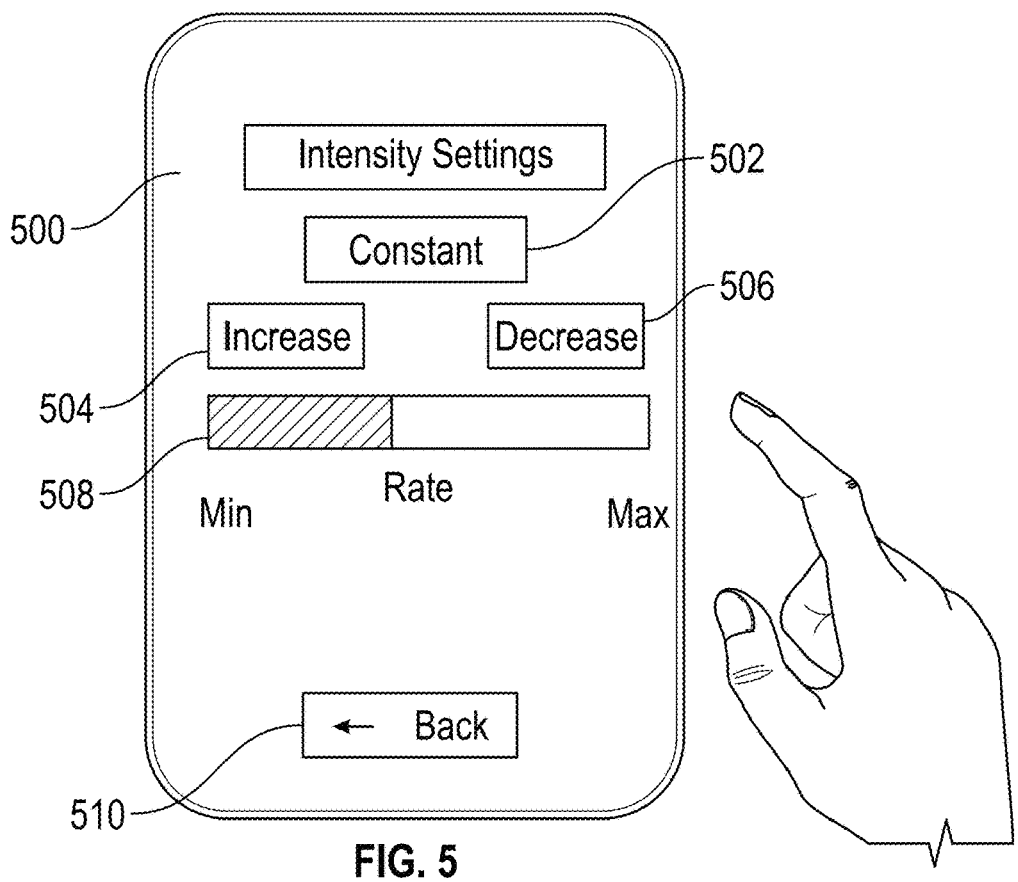
FIGS. 5-8 are illustrations of programming one parameter of the stimulation elements in accordance with a non-limiting embodiment.

FIG. 5 illustrates an example where the intensity button 402 has been activated by the individual. According to exemplary embodiments, the intensity of stimulation during the stimulation time period may be constant, gradually increasing or gradually decreasing. Accordingly, the intensity setting screen 500 include selection buttons for selecting (programming) constant 502, increasing 504 or decreasing 506 stimulation. In one non-limiting embodiment, when a user selects either the increasing button 504 or the decreasing button 506, a slide-bar adjustment area 508 become active so that the individual may drag an indicator from a minimum ("Min") setting to a maximum ("Max") setting as shown. Additionally, the intensity settings screen 510 presents individual with a touch-sensitive back button 510 to return to the setting screen 400 of FIG. 4.

Figure 6:
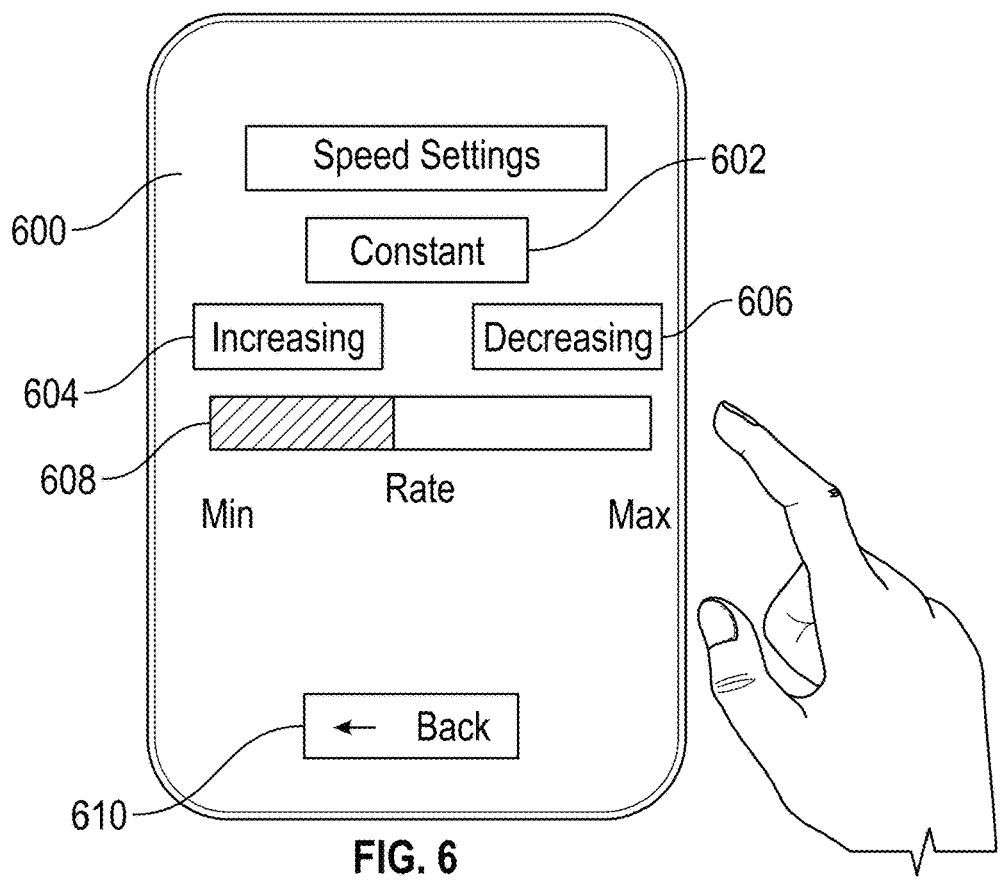

FIG. 6 illustrates an example where the speed button 404 has been activated by the individual. According to exemplary embodiments, the speed that the stimulation is applied during the stimulation time period may be constant, gradually increasing or gradually decreasing. Accordingly, the speed setting screen 600 include selection buttons for selecting (programming) constant 602, increasing 604 or decreasing 606 stimulation speed. In one non-limiting embodiment, when a user selects either the increasing button 604 or the decreasing button 606, a slide-bar adjustment area 608 become active so that the individual may drag an indicator from a minimum ("Min") setting to a maximum ("Max") setting as shown. Additionally, the speed settings screen 600 presents individual with a touch-sensitive back button 610 to return to the setting screen 400 of FIG. 4.

Figure 7:
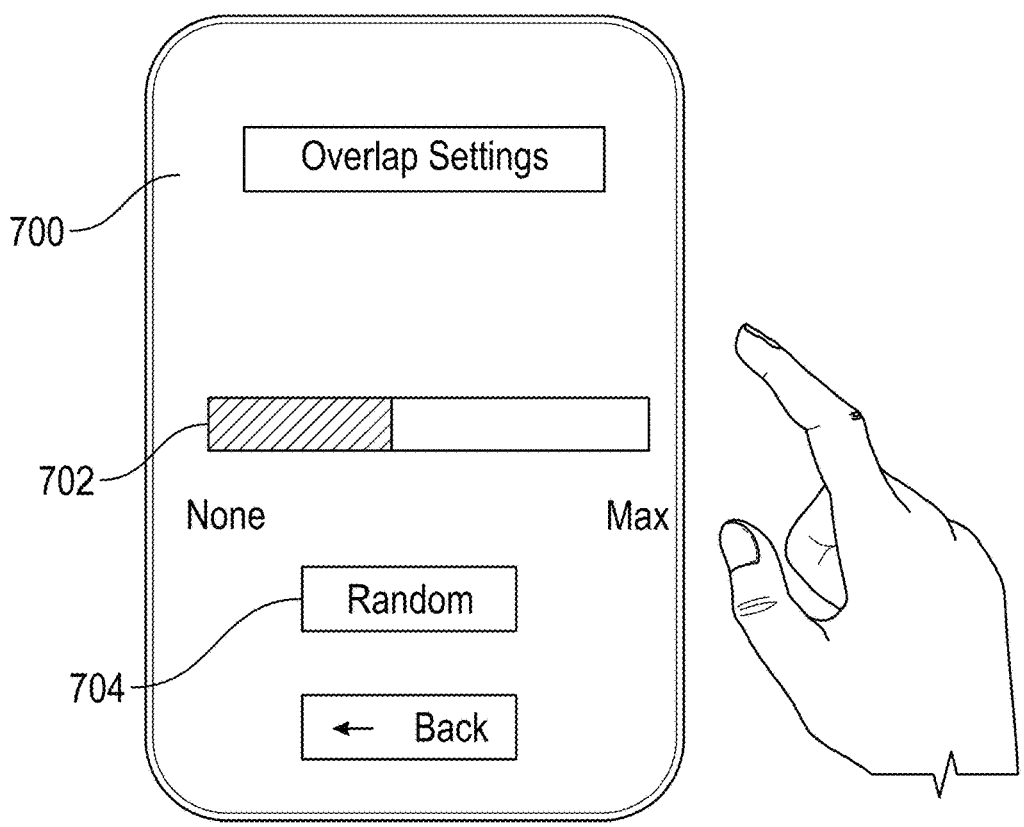
Figure 8:
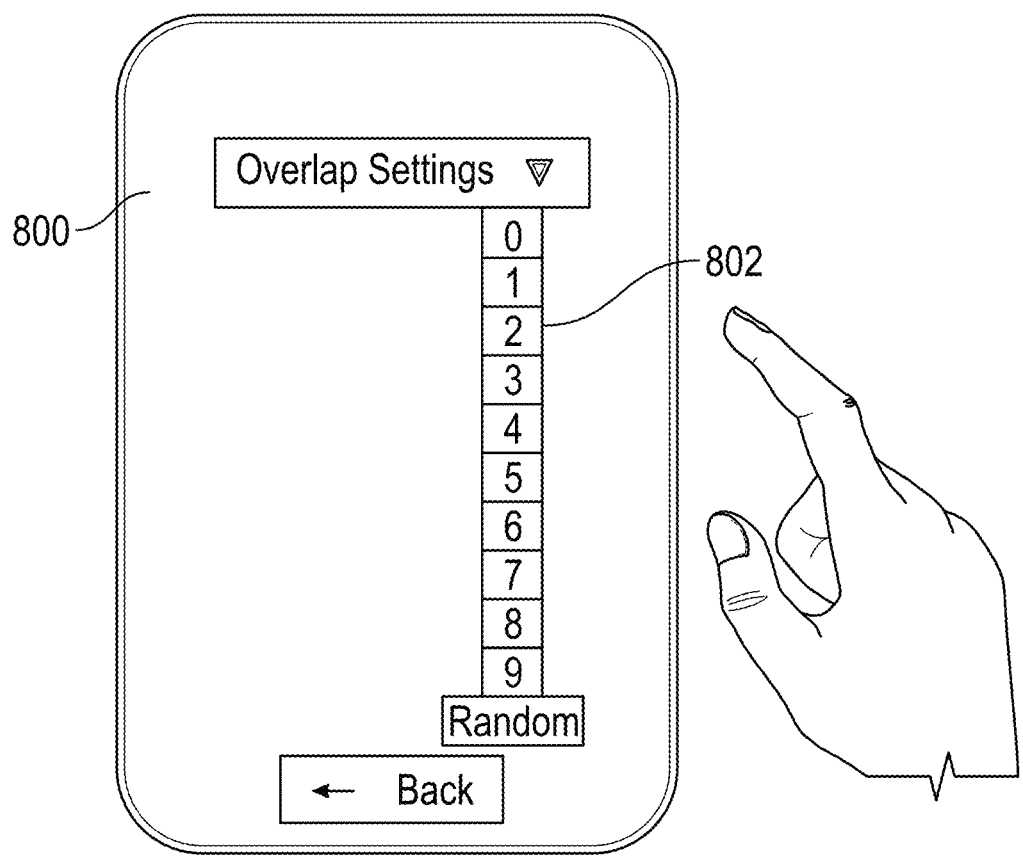

FIG. 7 illustrates an example where the overlap button 406 has been activated by the individual. In one non-limiting embodiment, the overlap settings screen 700 includes a slide-bar adjustment area 702 so that the individual may drag an indicator from a "none" setting (continuous bi-lateral stimulation mode) to a "maximum" overlap setting as shown. Additionally, the overlap settings screen 700 presents individual with a touch-sensitive randomize button 704. When the randomize button 704 is selected by the individual, the time period in which both vibrating elements 104 simultaneously vibrate is randomly selected by the controller (202 of FIG. 2) as will be discussed below. In FIG. 8, an alternate non-limiting embodiment of an overlap settings screen 800 is illustrated having a drop-down menu 802 in which the period of overlap ("0" being the continuous bi-lateral stimulation mode), or the random setting, may be selected by the individual. As will be appreciated by those skilled in the art, the screen format illustrated in FIG. 6 may also be used for adjusting the intensity setting (FIG. 5) and the speed setting (FIG. 6).

Figure 9A:
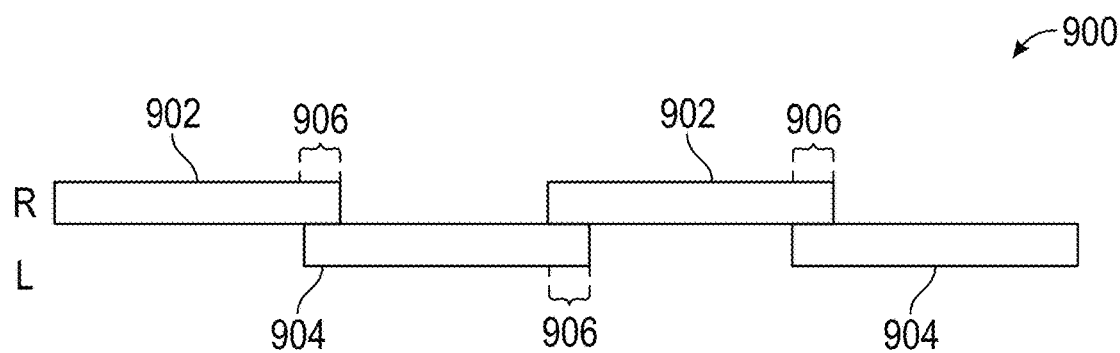
FIGS. 9A-9C are illustrations of timing diagrams for applying stimulation via the stimulation elements in accordance with non-limiting embodiments.
Figure 9B:
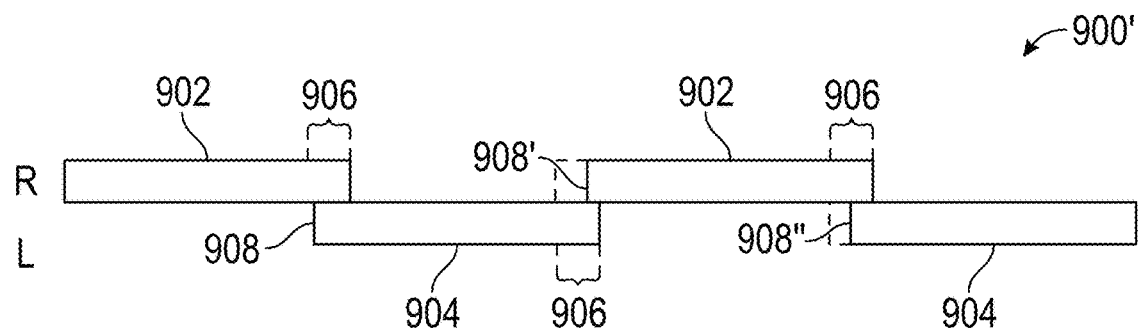

FIGS. 9A-9B are timing diagrams illustrating non-limiting embodiments of the alternating asynchronous bilateral stimulation as contemplated by the present disclosure. In FIG. 9A, a timing diagram 900 illustrates a time period 902 during which one of the vibrating elements 104 (designated "R" for a right side of an individual's body) is vibrating. Timing diagram 900 also includes a time period 904 during which the opposite side (designated "L" for a left side of an individual's body) vibrating element 104 is vibrating. An overlap time period 906 is also illustrated during which both vibrating elements 104 are simultaneously vibrating. In the embodiment of FIG. 9A, the duration of the overlap period 906 is programmed by the individual in any suitable manner, including the non-limiting examples provided in connection with FIGS. 7-8. In FIG. 9B, the randomize option has been selected by the individual (see 704 of FIG. 7) which causes the time period in which both vibrating elements are simultaneously vibrating to be randomly selected between vibrating cycles from one side of the individual's body to the bilateral (opposite) side. As an example, and not as a limitation, observing from the left-side to the right-side of FIG. 9B shows a leading-edge (meaning the beginning of the vibration period 904) 908 beginning at the maximum point (most amount of simultaneous vibration) of the overlap time period 906. The leading-edge 908' of time period 902 can be seen to have a shorter time of overlapping vibrations. Moving on, leading-edge 908" of time period 904 can be seen to begin at about the midpoint of the overlap time period 906. In the embodiment illustrated by timing diagram 900' the alternating vibrations would continue to randomly overlap within the overlap time period 906 until the individual deactivates the vibrating elements by controlling the mobile device 102.

Figure 9C:
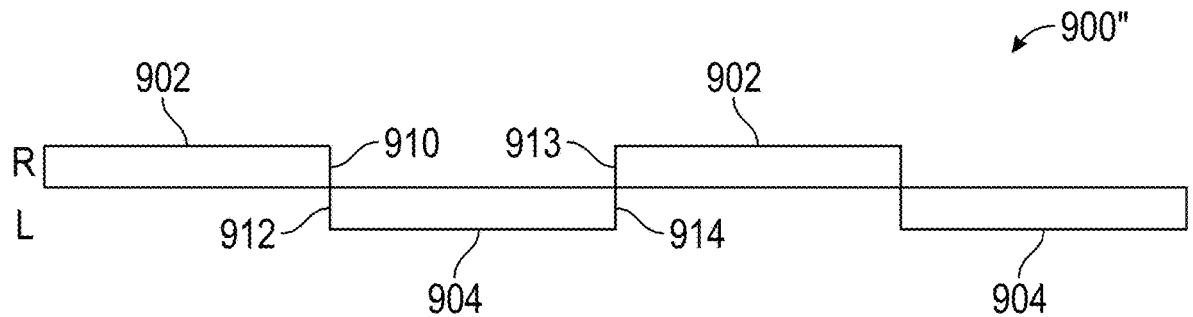

FIG. 9C is a timing diagram illustrating non-limiting embodiments of the alternating continuous bilateral stimulation as contemplated by the present disclosure. In FIG. 9C, a timing diagram 900" illustrates a time period 902 during which one of the vibrating elements 104 (designated "R" for a right side of an individual's body) is vibrating. Timing diagram 900" also includes a time period 904 during which the opposite side (designated "L" for a left side of an individual's body) vibrating element 104 is vibrating. As illustrated in FIG. 9C, at the conclusion (trailing edge 910) of the vibrating time period 902, the vibrating period 904 begins (leading edge 912) without pause or interruption in the simulation being applied to the individual. As such, this form of stimulation is said to be continuous bi-lateral stimulation. Similarly, at the conclusion (trailing edge 914) of the vibrating time period 904, the vibrating period 902 begins again (leading edge 916) also without pause or interruption in the simulation being applied to the individual.

Figure 10:
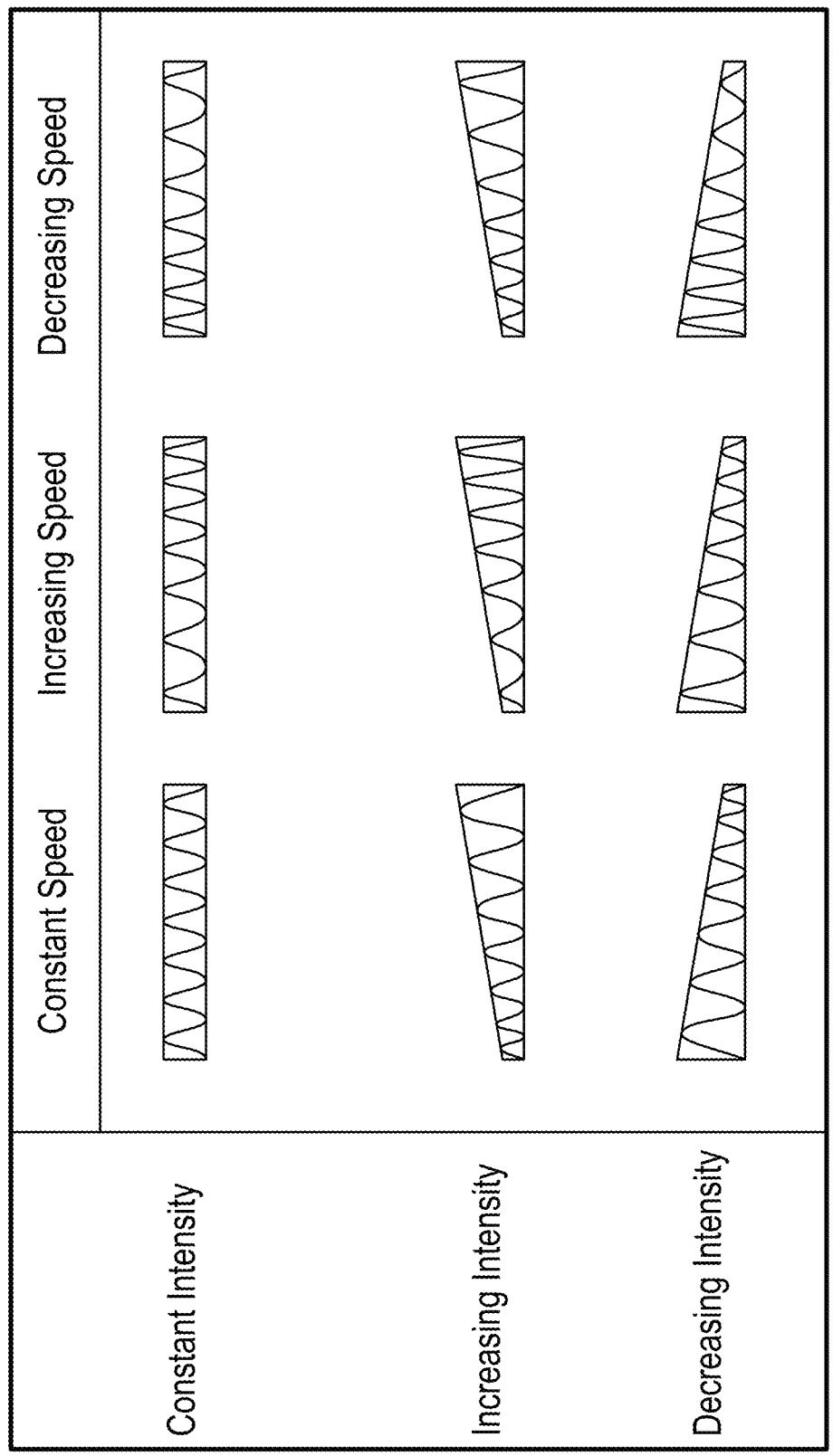
FIG. 10 are illustrations of various permutations of operating modes of the present disclosure in accordance with non-limiting embodiments.

FIG. 10 illustrates some of the possible operating modes of the system of the present disclosure to provide the therapeutic benefit afforded by the method disclosed herein. As discussed above in connection with FIGS. 9A-9C, one mode of operation focuses on whether the system is providing alternating asynchronous bilateral stimulation (fixed or random overlap) or alternating continuous bilateral stimulation (no gap or pause between left and right simulations). Additionally, as shown in FIG. 10, the intensity and the speed of stimulation may be constant, gradually increasing or gradually decreasing over the stimulation period leading to the nine operating modes illustrated in FIG. 10. A person can vary the settings (see, FIGS. 4-8 and associated text) to find the mode of operation that provides the greatest benefit to that person under the present circumstances.

Figure 11:
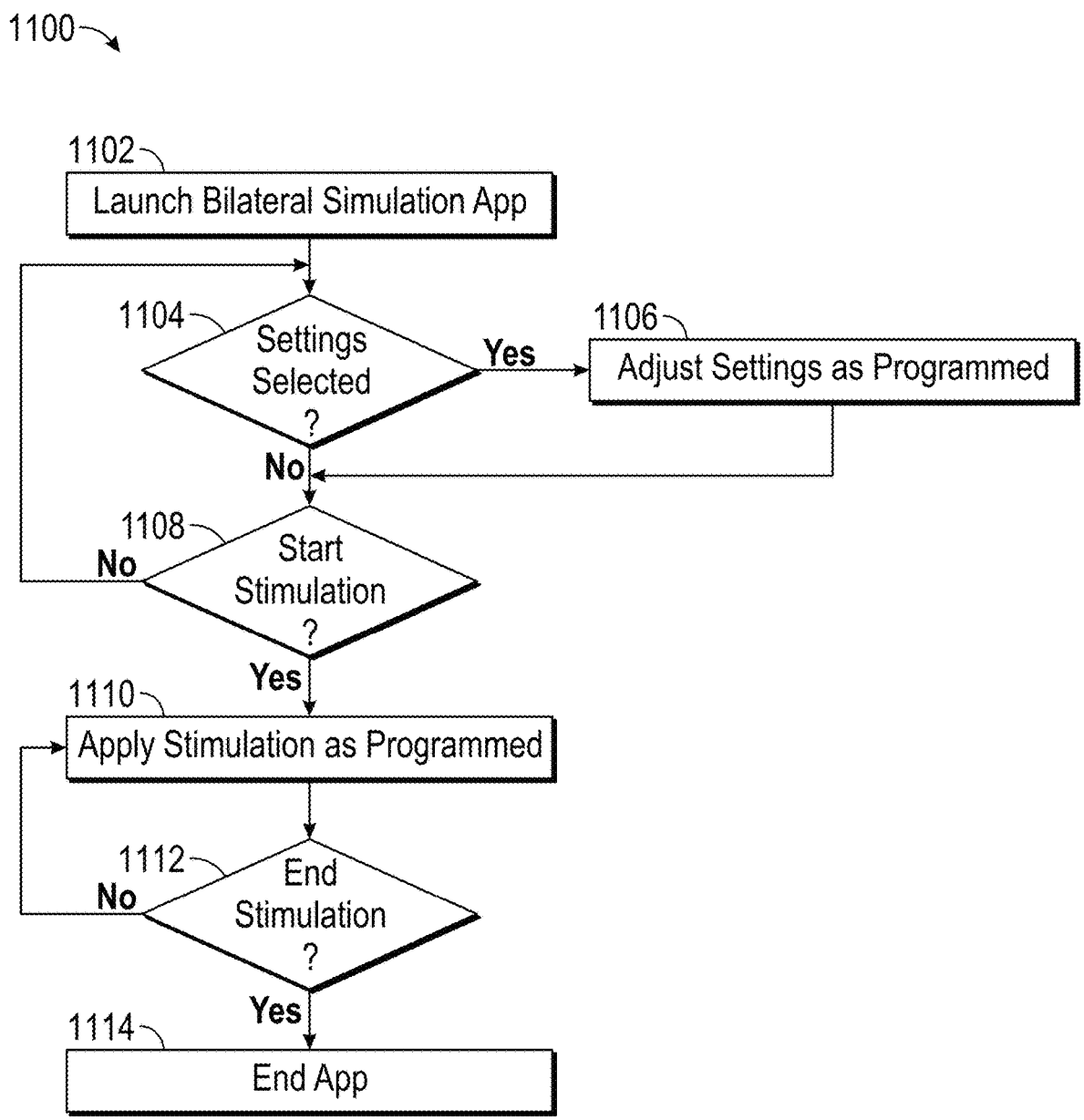
FIG. 11 is a flowchart of a method in accordance with a non-limiting embodiment.

FIG. 11 is a flow diagram of a method 1100 performed by the bilateral stimulation system in accordance with a non-limiting embodiment. In one embodiment, the various tasks performed in connection with the method 1100 of FIG. 11 are performed by instruction stored on a non-transitory computer medium being executed in a processing unit, hardware, firmware, or any combination thereof.

For illustrative purposes, the following description of the method 1100 of FIG. 11 refers to elements mentioned above in connection with FIG. 1 to FIG. 16.

It should be appreciated that the method of FIG. 11 may include additional or alternative tasks, or may include any number of additional or alternative tasks, and that the method of FIG. 11 may be incorporated into a more comprehensive procedure or process having additional functionality not described in detail herein or implemented as a stand-alone procedure. Moreover, one or more of the tasks shown in FIG. 11 are removable from an embodiment of the method 1100 of FIG. 11 as long as the intended overall functionality remains intact.

The method begins in block 1102 where the bilateral stimulation application (app) is launched (begun) on the mobile device 102 so that the individual may receive the asynchronous (or continuous) alternating bilateral stimulation as discussed above. In block 1104, a determination is made as to whether the individual has selected a settings feature to adjust the programming of the stimulation as discussed above in connection with FIGS. 4-8. If the determination of block 1104 is that the individual has elected to adjust the programming of the stimulation, the method proceeds to block 1106 where the settings are adjusted as desired by the individual as discussed above. Conversely, if the determination of block 1104 is that the individual has not elected to change the stimulation programming, the routine proceeds to block 1108 to determine whether the individual has activated the stimulation. If not, the routine loops around to block 1704 and routine continues. Assuming the determination of block 1108 is that the individual desires to commence simulation, the simulation is applied in asynchronous (or continuous) and alternate manner in block 1110 as discussed above. The stimulation can continue for a time period of until the individual decides to stop the stimulation as determined in block 1112, at which point the application ends in block 1114. Otherwise, the routine loops back to step 1110 and the stimulation is continued for a predetermined time period or for any time period desired by the individual.

Figure 12A:
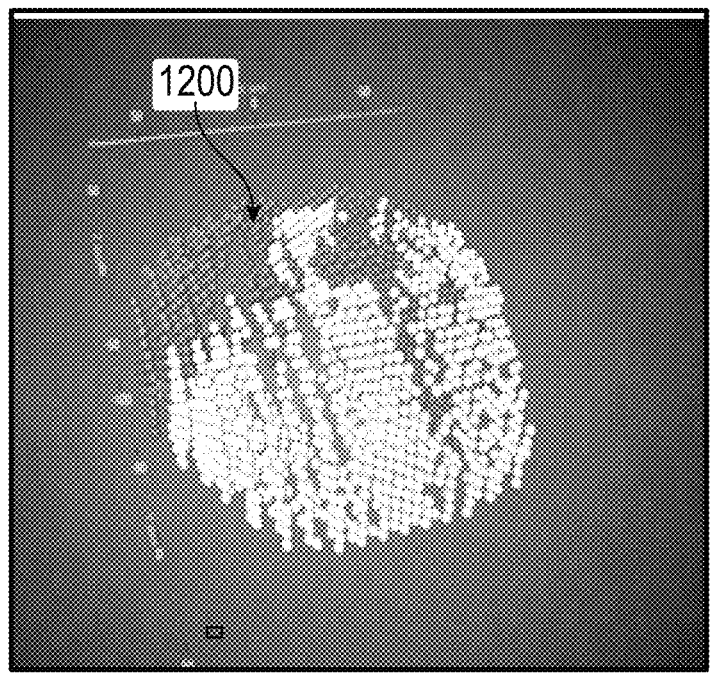
FIGS. 12A-12B are illustrations demonstrating the benefits of the present disclosure in accordance with non-limiting embodiments.
Figure 12B:
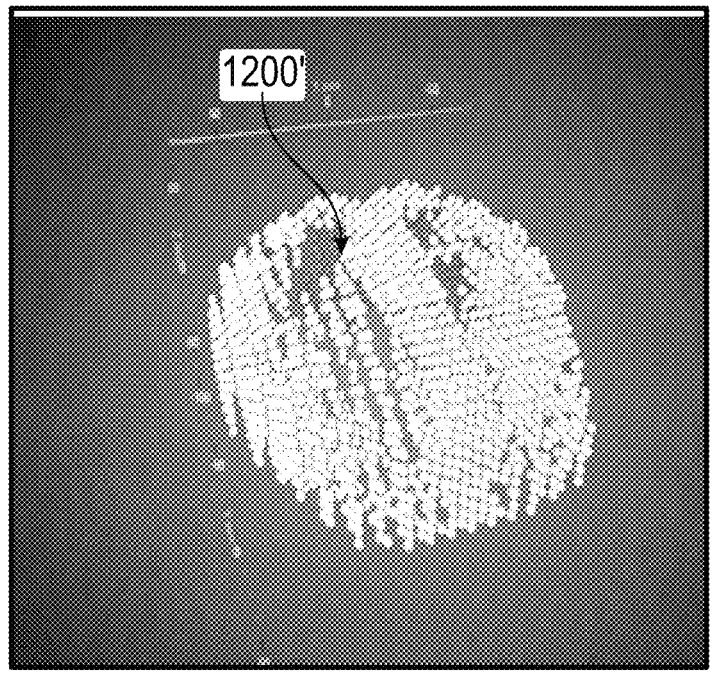

As a non-limiting practical example of the therapeutic benefits afforded by the present disclosure, FIGS. 12A-12B are brain images showing qEEG results using a Cognionics Quick-20 Dry Headset, Neuroguide (version 2.8.7), and LFT Tools Software for analysis. In this example, the person is a 38 year old male CEO experiencing excess beta activity 1200 as seen in FIG. 18A. After thirty second of applied therapeutic treatment according to the present disclosure (person eyes open in a resting state condition), is significantly reduced 1200' demonstrating the significant advantages of the present disclosure. Additionally, other objective tests can verify the therapeutic benefit afforded by the present disclosure. Non-limiting examples of such test include, motor control tests, cognitive state tests, cognitive ability tests, sensory processing tests and performing standardized cognitive tasks.

Figure 13:
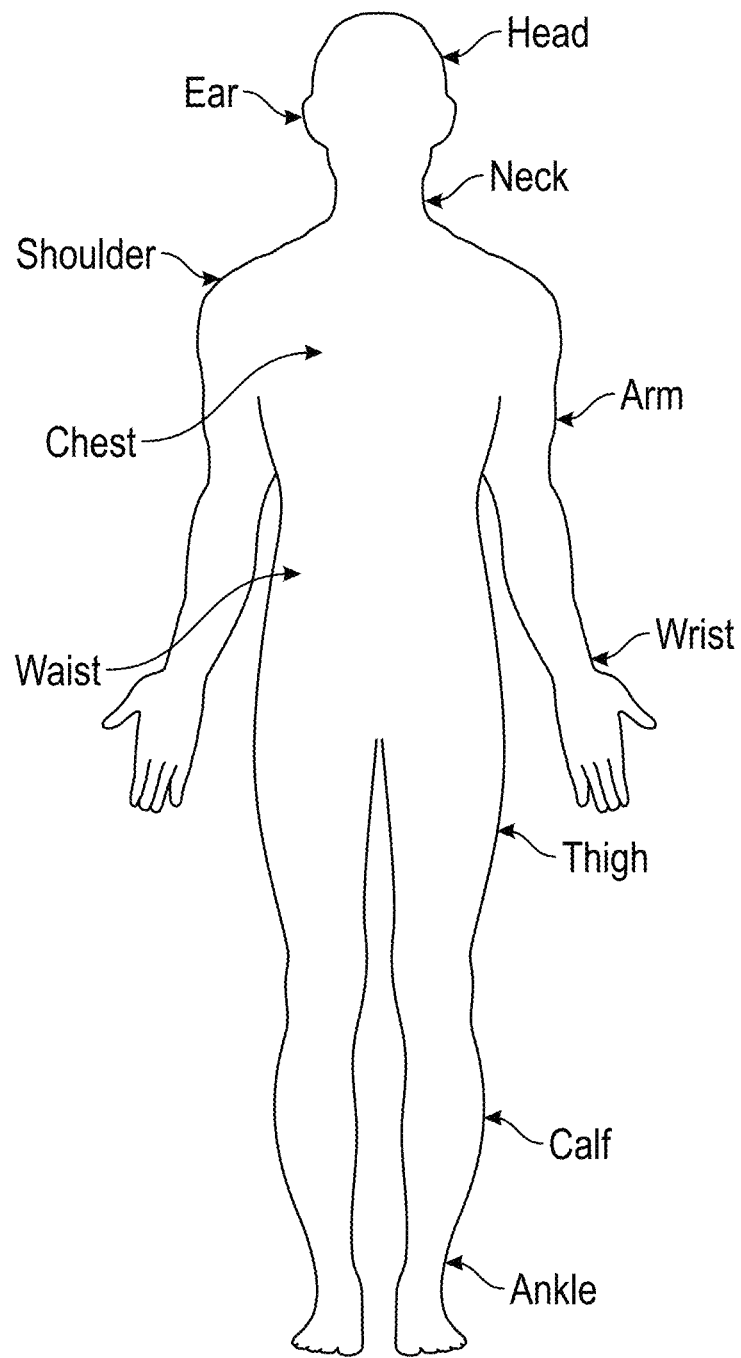
FIG. 13 is an illustration of an individual showing exemplary positions for the stimulation elements in accordance with non-limiting embodiments.

FIG. 13 is a line-drawing of an individual's body illustrating various non-limiting positions were a vibrating element 104 may be positioned. As used herein, a vibrating element 104 being brought into position or placed on individual body means being brought into "therapeutic contact" with an individual's body. Therapeutic contact may be achieved by direct contact (e.g., hand held, secured via adhesive or placed via a strap) or via indirect contact (e.g., through clothing, a coupling gel, through a wearable device or through interaction with articles of daily life having the vibrating elements incorporated in them as will be discussed below). Accordingly, therapeutic contact means only that the individual need be able to perceive the stimulation provided by the bilateral vibrating elements 104 during therapy.

Figure 14:
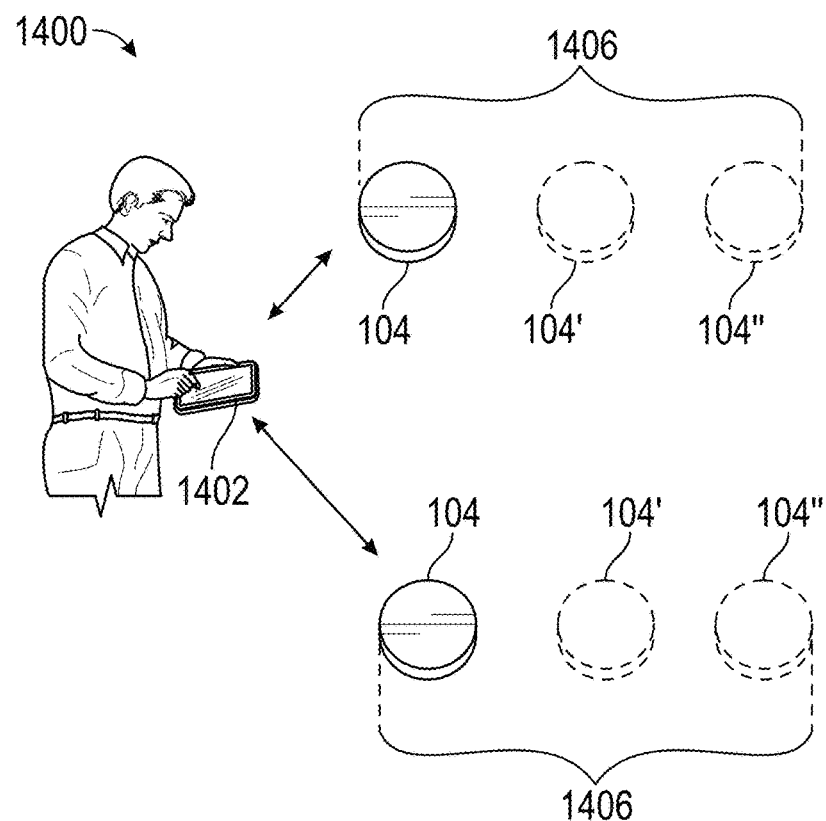
FIG. 14 is an illustration of an alternate embodiment employing multiple stimulation elements in arrays positioned on either lateral side of an individual in accordance with a non-limiting embodiment.

With continued reference to FIGS. 1-11, Referring now to FIG. 14, an alternate non-limiting embodiment of an asynchronous bilateral stimulator 1400 is shown. In the embodiment of FIG. 14, multiple vibrating elements 104, 104' and 104" are arranged in vibrating arrays 1406 such that multiple vibrating elements may be placed at various bilateral points on an individual's body or incorporated at various places in articles of daily life as will be discussed below. Those skilled in the art will appreciate that more or fewer vibrating elements 104 may be used in any particular vibrating array 1406. In operation, the mobile device 1402 communicates wirelessly with each vibrating element in vibrating array 1406 causing one array to vibrate for a time period, then both arrays to vibrate simultaneously for an overlap period, and then the alternate array to vibrate for the time period. In various non-limiting embodiments, the time period of vibration, the intensity of the vibration and the overlap time period are programmable by the individual as discussed above.

Figure 15:
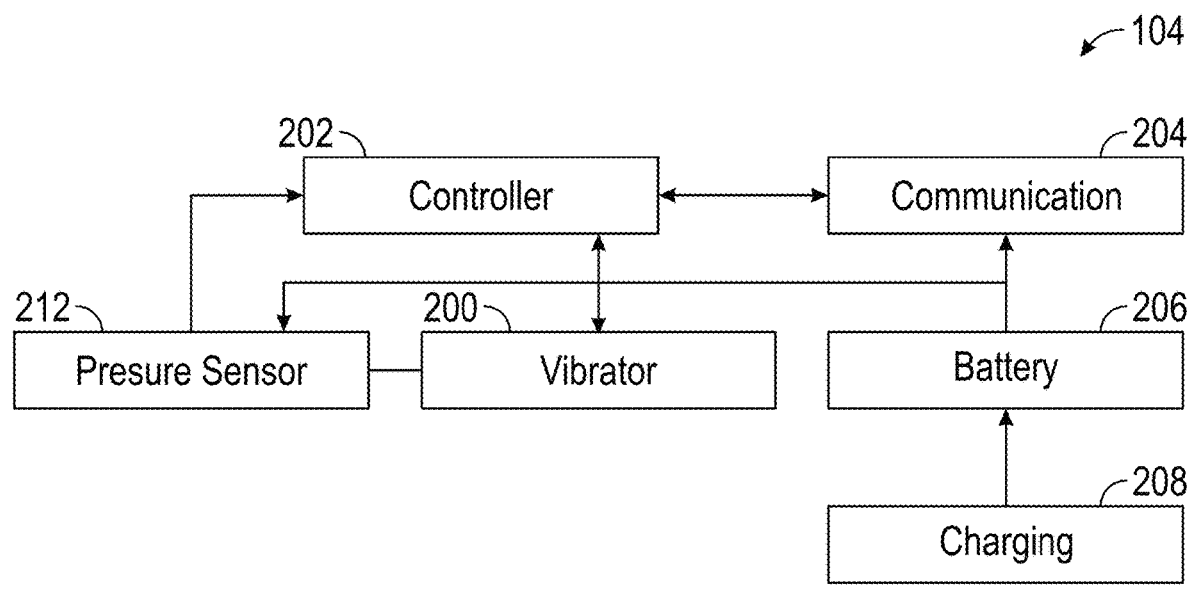
FIG. 15 is a block diagram of an alternate implementation of the arrayed stimulation elements of FIG. 14 in accordance with a non-limiting embodiment.

FIG. 15 is a block diagram of an alternate embodiment of the stimulation (vibrating) elements 104 that offers an advantage in the multiple stimulator array embodiment of FIG. 14. The basic operation of the vibrating element 104 of FIG. 15 is the same as described in connection with FIG. 2 above, with the addition of a pressure sensor 212. In a bilateral stimulation element array 1406, it is contemplated that only one or a few of the vibrating elements 104 in the stimulation array 1406 may be in therapeutic contact with the individual. Accordingly, the present disclosure contemplates that in some embodiments, only the stimulation elements (e.g., 104, 104', 104") having a sufficient pressure indication would vibrate when instructed to by the mobile device 1402. This operation offers the advantage of conserving battery power by not having vibrating elements 104 that are not in therapeutic contact with the individual to vibrate. In other embodiments, each pressure sensor in the array 1406 reports it's pressure indication detected by the pressure sensor 212 to the mobile device 1402, which in turn instructs only those pressure sensors having a sufficient pressure rating to vibrate to provide the therapeutic benefit to the individual. In this way, as the individual moves or changes position, different vibrating elements 104 of the vibrating array 1406 may come into therapeutic contact with the individual and therefore provide the therapeutic benefit to a non-stationary person.

Figure 16:
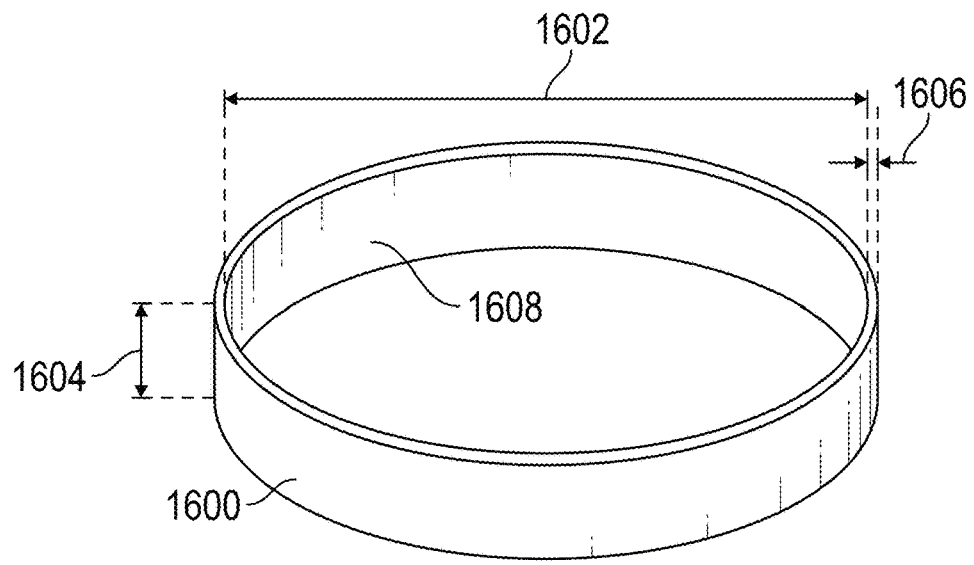
FIG. 16 is an illustration of a securing band that can be used with the stimulation elements in accordance with a non-limiting embodiment.
Figure 17A:
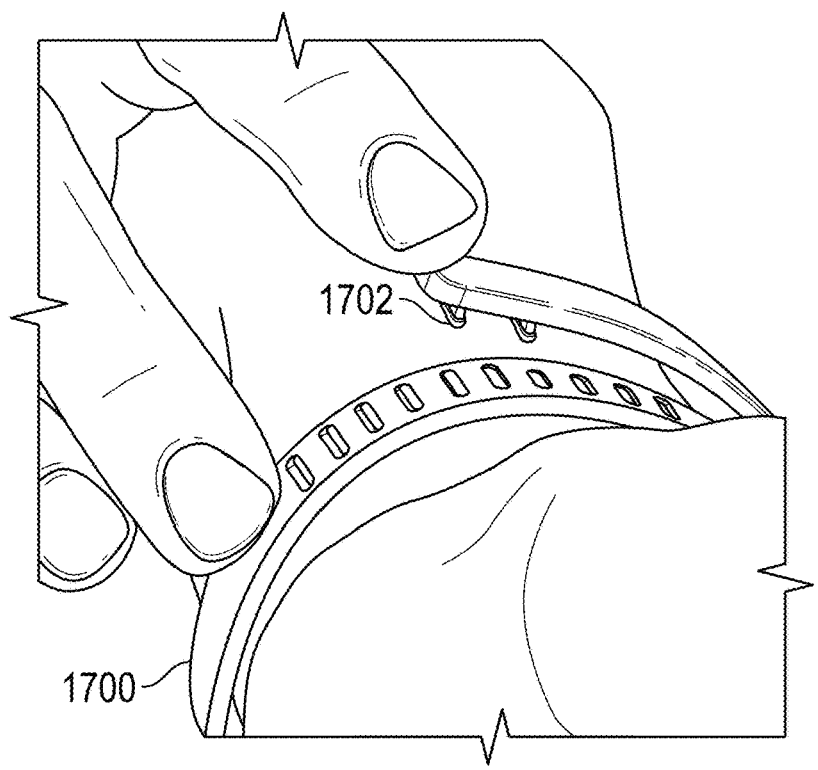
FIGS. 17A-17B are illustrations of an adjustable wristband that can be used with the stimulation elements in accordance with a non-limiting embodiment.
Figure 17B:
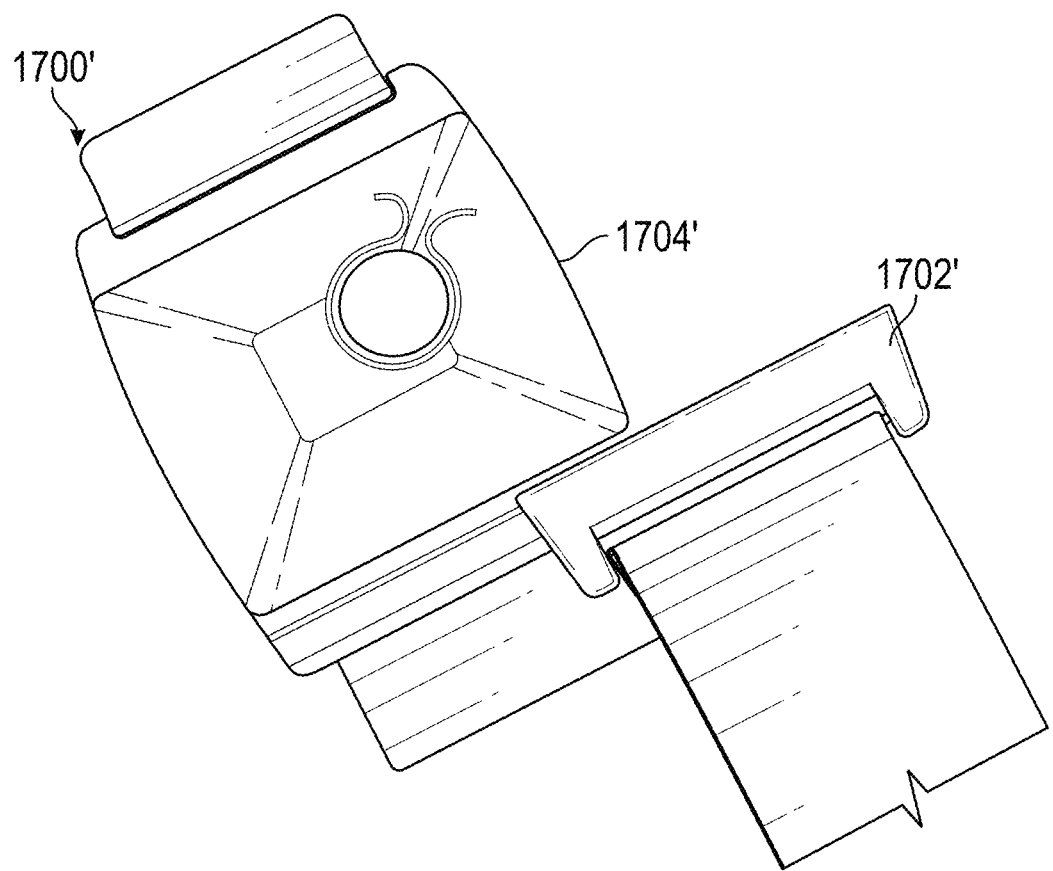

The present disclosure contemplates that the bilateral stimulation system 100 can provide therapeutic benefit to both stationary and mobile individuals. For example, stationary individuals can simply hold the vibrating elements 104 in the person's hand during a therapeutic session. In other embodiments, the vibrating elements need to be positioned on the individual in a manner that promotes the individual's mobility. Accordingly, FIGS. 16-19 illustrate non-limiting techniques for positioning a vibrating element 104 on an area of an individual's body. In FIG. 16, a securing band 1600 is shown. The securing band 1600 may be compliant, elastic or may be secured using a hook-and-eye arrangement as is known in the art. The securing band 1600 has a diameter 1602, a height 1604 and a thickness 1606 sized suitably for the area of the individuals body (e.g., wrist, arm, chest, leg, ankle) that the band 1600 will be placed around. The thickness 1606 is also selected to facilitate attachment of the vibrating element 104 by the clip 300 (see FIG. 3A). The securing band 1600 has an interior surface 1608 upon which a material can be placed for the individual's comfort or to absorb moisture. In FIG. 17A, a wristband 1700 is illustrated that may be used to position the vibrating elements 104 about an individual's wrist. The wristband 1700 has an attachment mechanism 1702 for securing the vibrating element 104 to the individual's wrist (for example). The attachment mechanism 1702 may be any suitable attachment mechanism such as those used to attach a wristwatch or fitness monitor to a person's wrist, ankle, waist, chest, etc. In FIG. 17B, a wristband 1700' is illustrated for positioning a vibrating element 1704 about an individual's wrist. The wristband 1700' has a sliding attachment mechanism 1702' for securing the vibrating element 1704 to the individual's wrist. The wristband 1700 or 1700' may be formed of plastic, leather, fabric, metal or other suitable material and may be designed to be worn casually or as a fashion accessory. In this way, a mobile individual can gain the advantage of the therapeutic benefit at any time during the day, evening or during a specific event by activating the stimulation elements 104 via the mobile device 102.

Figure 18:
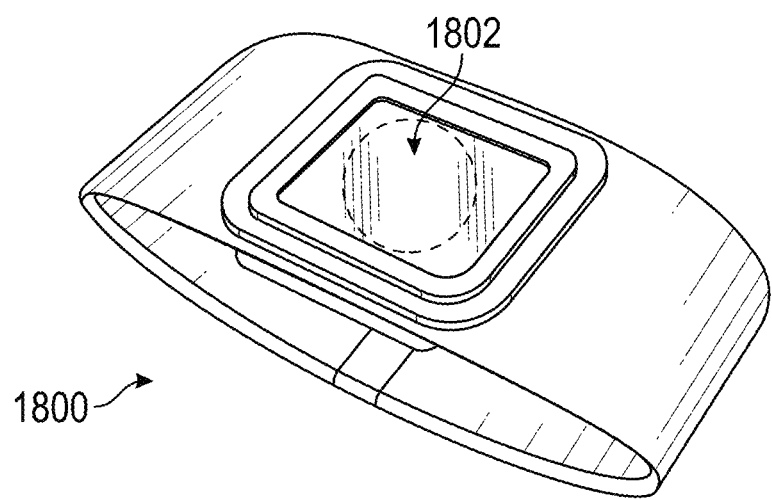
FIG. 18 is an illustration of a fitness monitor for use with the stimulation elements in accordance with a non-limiting embodiment.
Figure 19:
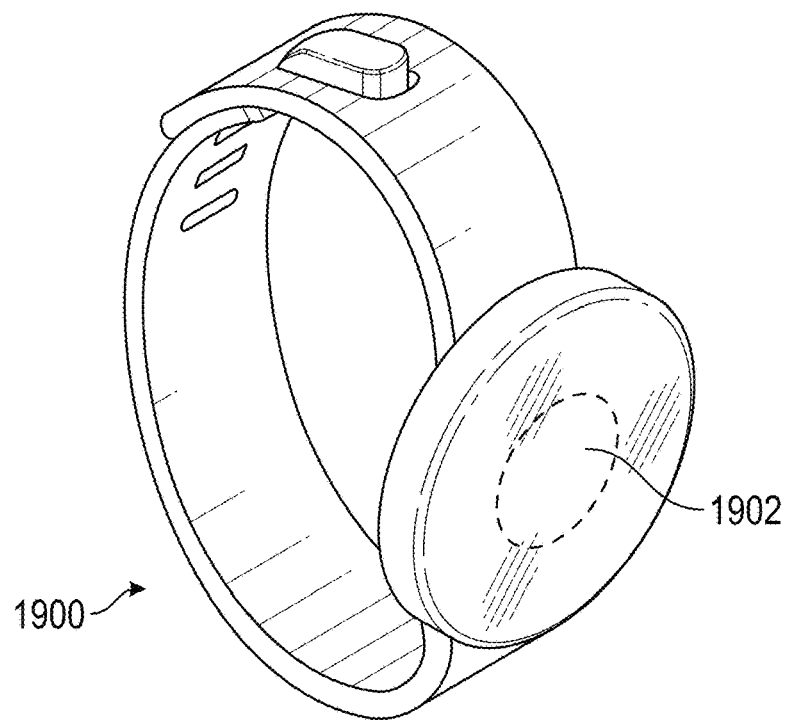
FIG. 19 is an illustration of a wristwatch for use with the stimulation elements in accordance with a non-limiting embodiment.

The vibrating elements 104 may also be combined into other devices used in daily life. For example, FIG. 18 illustrates a wrist-worn fitness monitor 1800 that includes a recess 1802 on the interior portion of the device sized suitably to receive a vibrating element 104. The vibrating element 104 may be placed in the recess 1802 by a friction-fit arrangement or by use of a removable adhesive disc (see FIG. 3B). Similarly, FIG. 19 illustrates a wristwatch 1900 having a recess 1902 on an interior portion to receive the vibrating element 104 as described above. In this way, one of the bilaterally positioned vibrating elements 104 can be integrated into an article of daily life and the opposite bilateral vibrating element can be positioned on the individual buyer the band embodiments discussed above in connections with FIGS. 16-17.

As discussed above, the present disclosure contemplates that many individuals would benefit by being able to use the bilateral stimulation system 100 at any time the individual desires. Non-limiting examples include while the individual is driving or commuting, at the office, during lunch, during a phone conversation, while watching or participating in an activity, or while relaxing and watching a movie or television. Accordingly, the present disclosure contemplates that the bilateral stimulation elements 104 can be readily integrated into articles of daily life that support both a mobile, stationary and par-stationary individual. In this way, the individual can activate stimulation elements 104 by the mobile device 102 at any time, and for as so much time, as the individual has to receive the therapeutic benefit. Following are non-limiting examples of various embodiments and applications for using the bilateral stimulation system 100 by incorporating the stimulation elements 104 into various articles of daily life.

Wearable Articles.

Figure 20A:
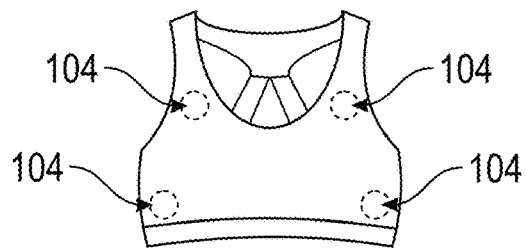
FIGS. 20A-20C, FIGS. 21-23 and FIGS. 24A-24(B) are illustrations of wearable embodiments incorporating bilateral stimulation elements in accordance with a non-limiting embodiment.
Figure 20C:
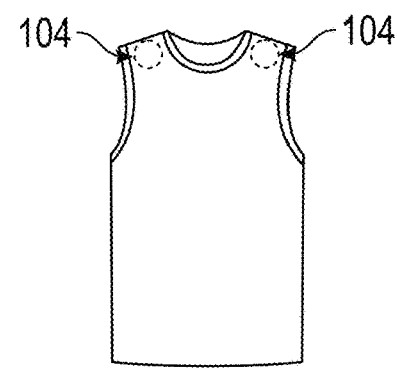
Figure 20B:
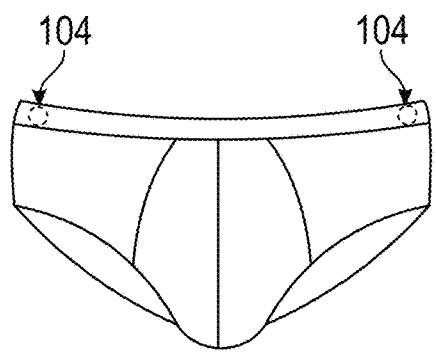

The present disclosure contemplates that the stimulation elements 104 may be integrated into wearable articles that bring the stimulation elements 104 into therapeutic contact with the individual wearing the article. Non-limiting examples of such garments include snug-fitting clothing or portions of wearable garments that are naturally in therapeutic contact with the individual such as by the force of gravity. As used herein, a "snug-fitting" garment includes, but is not limited to, an elasticized garment or an elasticized portion of a garment. For example, undergarments typically are snug-fitting and include, but are not limited to, a sports bra as shown in FIG. 20A having stimulating elements 104 bilaterally positioned in two exemplary locations. The stimulation elements 104 can be activated individually or as part of the stimulation array as discussed above in connection with FIG. 14. As another example, men's or women's (boys or girls) underwear may have stimulation elements in the waistband as shown in FIG. 20B. Additionally, T-shirts, camisoles or similar undergarments may have vibration elements 104 positioned in a shoulder strap or shoulder area of the garment (as illustrated in FIG. 20C) that are naturally in therapeutic contact with the individual wearing the garment due to the force of gravity.

Figure 21:
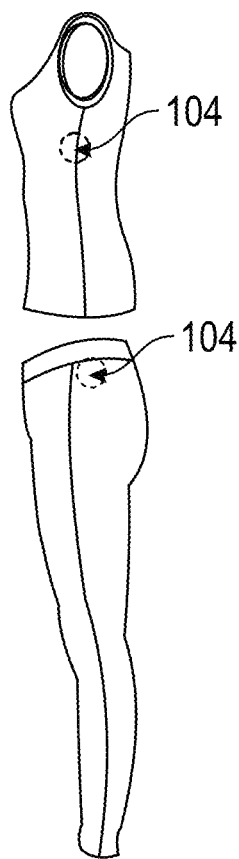
Figure 22:
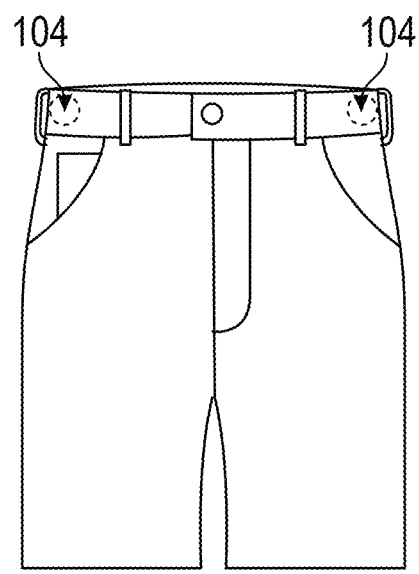
Figure 23:
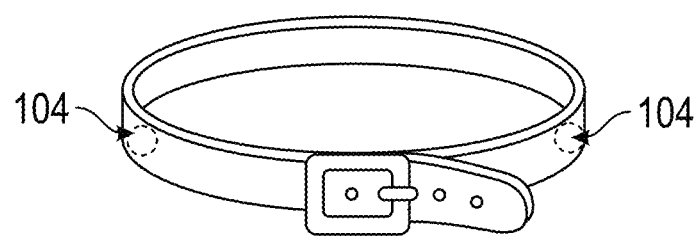
Figure 24A:
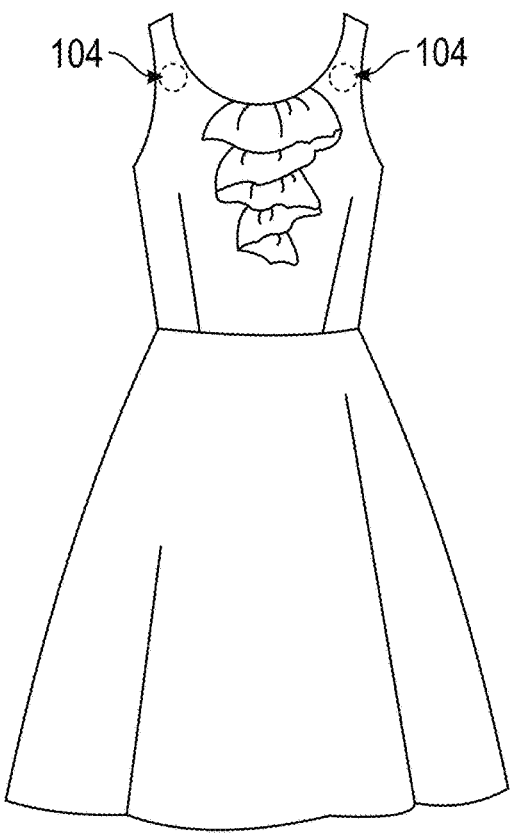
Figure 24B:
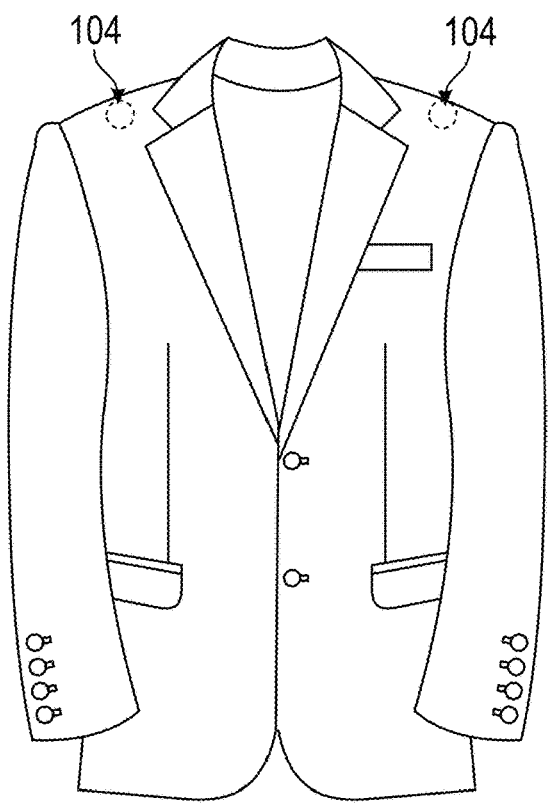

Outerwear garments can also have stimulation elements 104 incorporated therein in positions that bring the stimulation elements into therapeutic contact with the individual. For example, swimwear or garments typically worn for yoga or other exercise activities are commonly snug-fitting and may have stimulation elements 104 positioned as illustrated in FIG. 21. Outerwear garments may have stimulation elements 104 positioned in waistbands as illustrated in FIG. 22. Additionally, accessories such as suspenders or belts (FIG. 23) may have stimulation elements positioned in them to be brought into therapeutic contact when worn by an individual. Moreover, casual wear, business wear and formalwear may have stimulation elements incorporated into them for women (FIG. 24A) or men (FIG. 24B). When the stimulation elements are incorporated into wearable articles, it may be advantageous in some embodiments to have the stimulation elements 104 be waterproof (e.g., hermetically sealed) so that the garment may be periodically laundered without having to remove the stimulation elements. Alternately, the stimulation elements 104 may reside in slots or pockets built into the garments so that they may be removed before laundering. In other embodiments stimulation elements 104 may be affixed to the garments such as by adhesive disc or a hook-and-eye fastening system.

Foot-Worn Articles.

Figure 25:
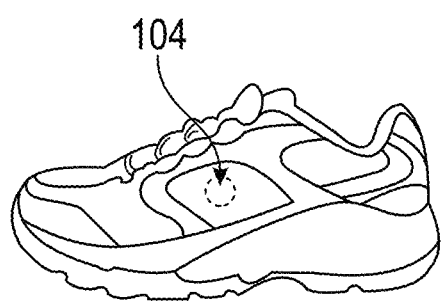
FIGS. 25-26, FIGS. 27(A)-27(B) and FIGS. 28(A)-28(B) are illustrations of footwear embodiments incorporating bilateral stimulation elements in accordance with a non-limiting embodiment.
Figure 26:
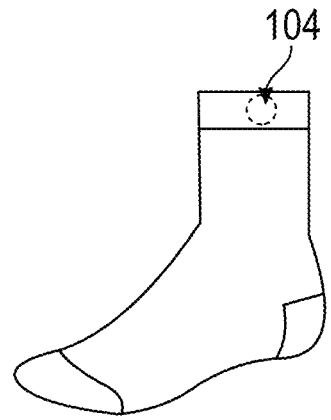
Figure 27A:
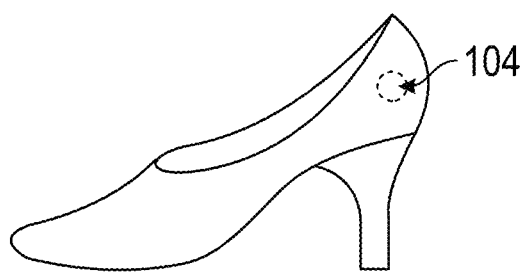
Figure 27B:
Figure 28A:
Figure 28B:

Footwear provides another opportunity for incorporating the stimulation elements 104 of the bilateral stimulation system 100 into the daily life of individuals. For example, FIG. 25 illustrates that the stimulation element 104 may be incorporated into a gym, tennis or sports shoe. It will be appreciated that various embodiments of socks (FIG. 26) provide snug-fitting footwear for incorporation of the stimulation elements 104. In addition to various forms of athletic wear, women's (FIG. 27A) or men's (FIG. 27B) casual, business or formal footwear may have the stimulation elements 104 incorporated into them. Also, various embodiments of boots may have the stimulation elements 104 incorporated into them. Non-limiting examples include military or construction boots (FIG. 28A) or "cowboy boots" as illustrated in FIG. 28B. Generally, will be appreciated that a wide variety of footwear and various embodiments of socks, whether or not worn with footwear, provide a useful means of bringing the stimulation elements 104 into therapeutic contact with an individual.

Head-Worn Articles.

Figure 29A:
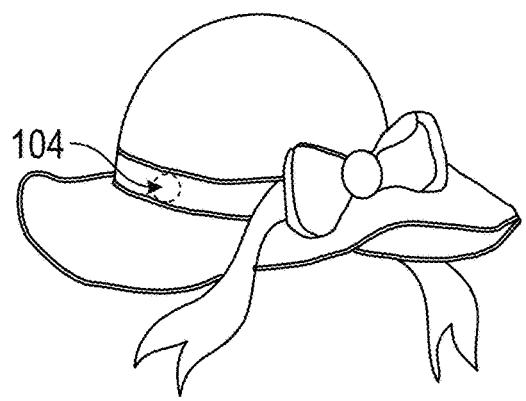
FIGS. 29(A)-29(B), FIGS. 30(A)-30(B), and FIGS. 31-40 are illustrations of head-worn embodiments incorporating bilateral stimulation elements in accordance with a non-limiting embodiment.
Figure 29B:
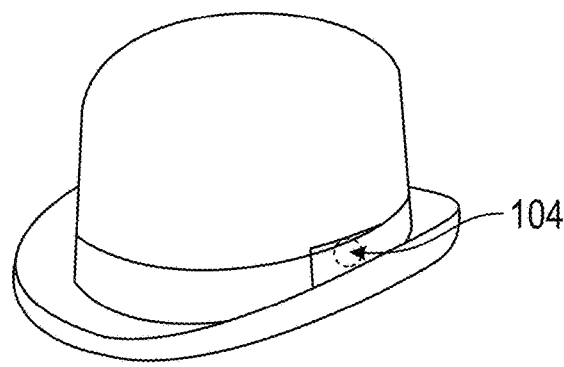
Figure 30A:
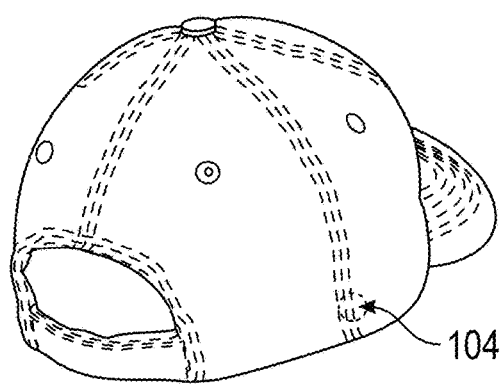
Figure 30B:
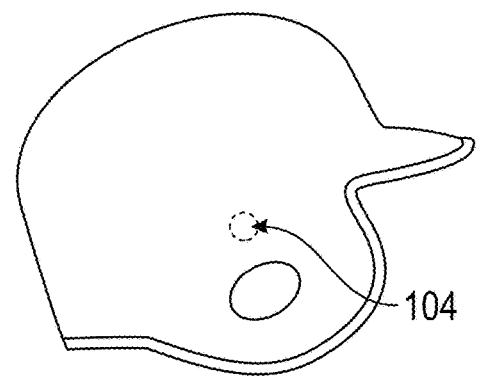
Figure 31:
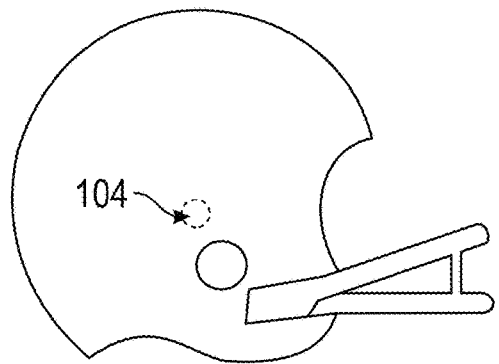
Figure 32:
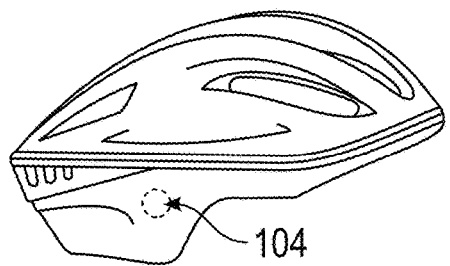
Figure 33:
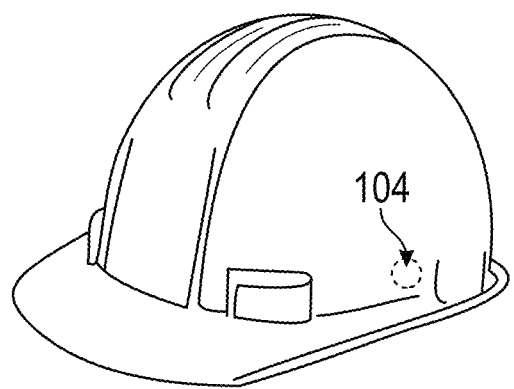
Figure 34:
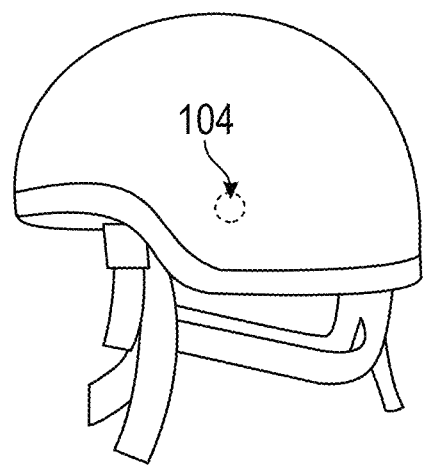

Head-worn articles are another category of wearable articles that provide a wide variety of implementations that support the incorporation of the stimulation elements 104. For example, women's (FIG. 29A) and men's (FIG. 29B) casual or formal hats may incorporate the stimulation elements 104 into the headband area thereof for use by the individual at any particular time. Moreover, "baseball" caps are commonly worn by a wide variety of individuals for both sports activities and as casual wear. The stimulation elements 104 may be incorporated into a variety of embodiments of baseball caps as illustrated in FIG. 30A. In addition, in a sports embodiment for baseball, stimulation elements 104 may also be integrated into batting helmets as illustrated in FIG. 30B, to reduce stress of the individual at-bat during a baseball game. As will be appreciated, an individual involved in any sports activity that involves some form of headwear may benefit from reduced stress and improve performance by having the stimulation elements 104 incorporated into the headwear appropriate for that sports activity. For example, FIG. 31 illustrates the stimulation elements 104 incorporated into a football helmet, while FIG. 32 illustrates the stimulation helmets 104 incorporated into a cycling helmet. Aside from sports activities, the stimulation elements 104 may be incorporated into construction helmets as shown in FIG. 33. Moreover, military personnel are often subject to high stress situations and may benefit from the stimulation elements 104 being incorporated into a variety of military headwear as illustrated in FIG. 34. Generally, ground, air and sea military personnel typically have some form of headwear into which the stimulation elements 104 can be incorporated.

Figure 35:
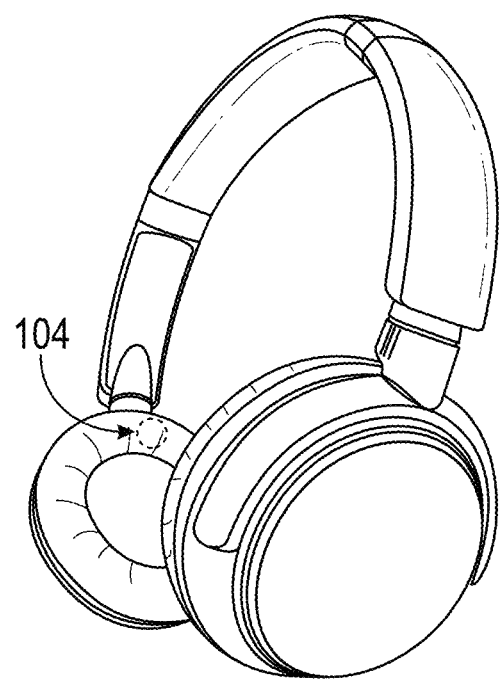
Figure 36:
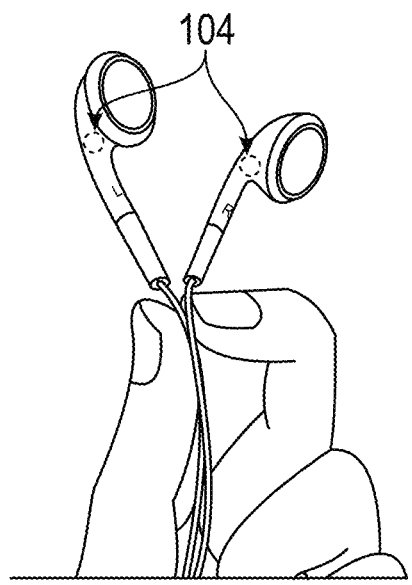
Figure 37:
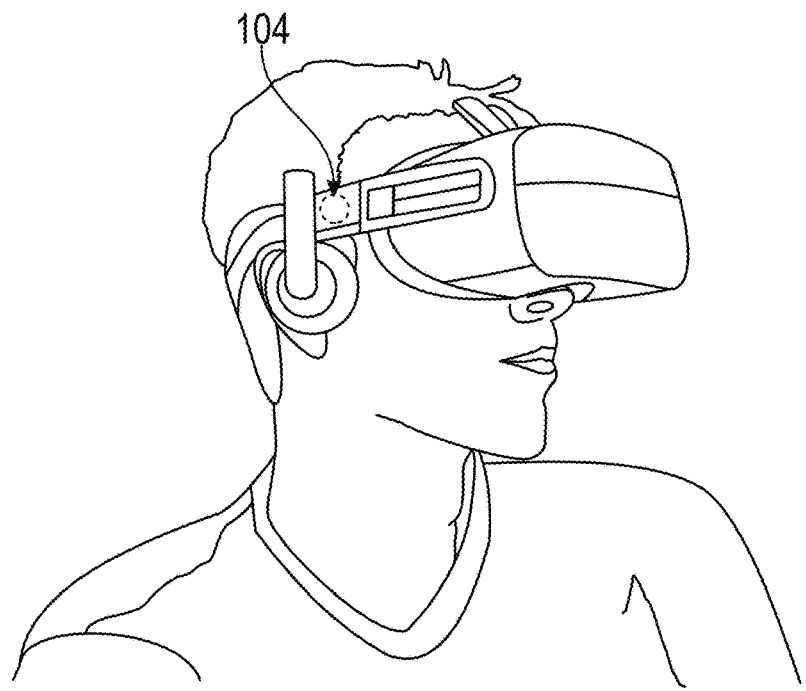
Figure 38:
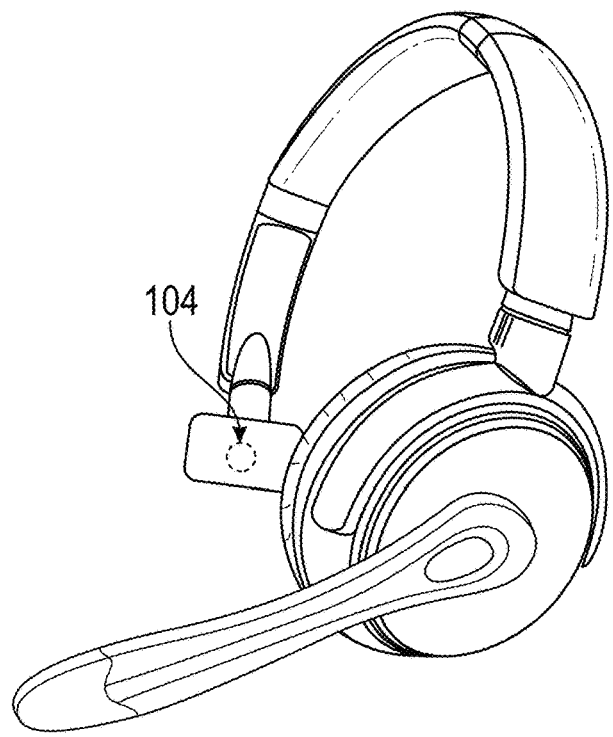
Figure 39:
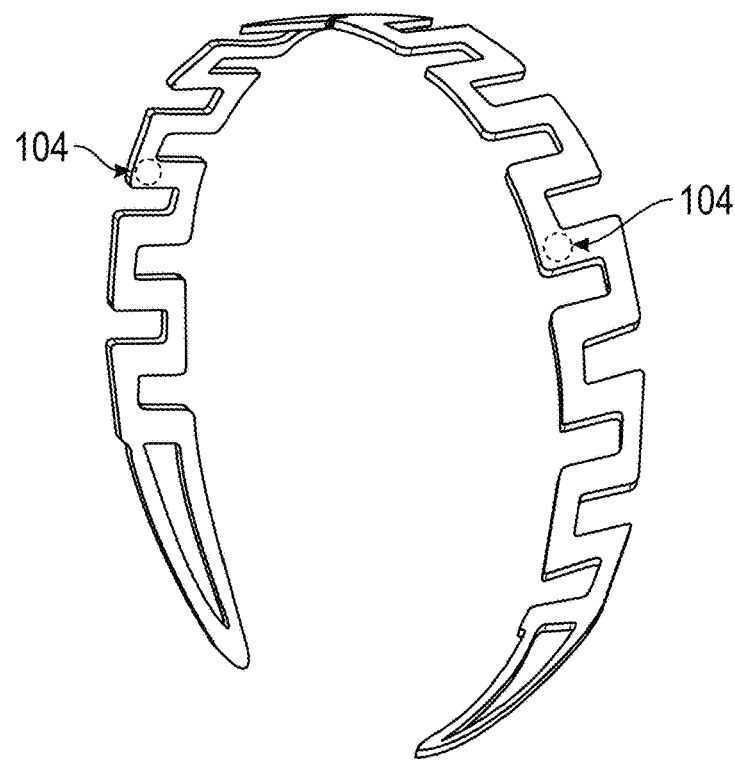
Figure 40:
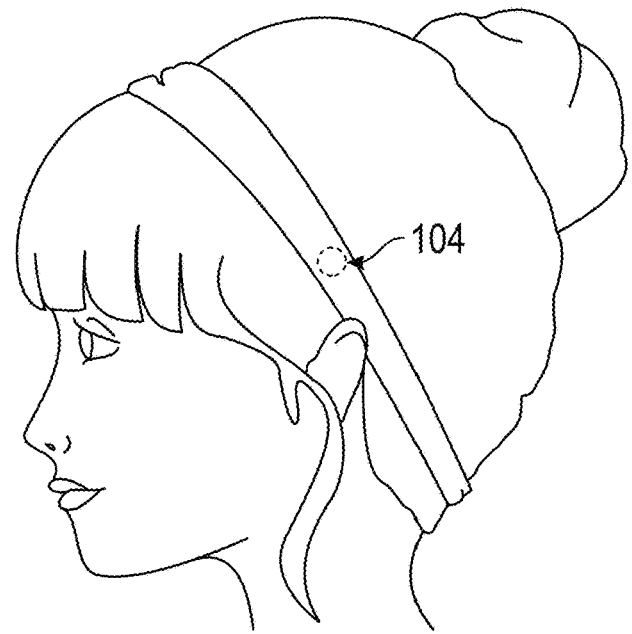

In addition to caps, hats and helmets, other head-worn articles are utilized by individuals for entertainment or other purposes. For example, FIG. 35 illustrates headphones that may be worn by an individual having the stimulation element 104 incorporated into the ear cuff of the headphones. Similarly, stimulation elements 104 may be incorporated into ear buds as shown in FIG. 36. In this way, relaxing sounds or music may be used in conjunction with the vibratory stimulation provided by stimulation elements 104 during the therapy session. Other entertainment embodiments such as virtual reality headwear may have stimulation elements 104 incorporated therein as illustrated in FIG. 37. In this way, individuals involved in virtual reality and augmented reality gaming can be provided with the therapeutic benefit to reduce stress and increase concentration while playing a virtual reality game. Additionally, coaches headsets commonly used in collegiate and professional football may have stimulation elements incorporated them as illustrated in FIG. 38. One stimulation element can be placed into the earpiece as illustrated in FIG. 35 and other stimulation element bilaterally positioned in the headpiece as illustrated in FIG. 38. In this way, both players (see FIG. 31) and the coaching staff may receive the therapeutic benefit provided by the present disclosure during a football game or other sport. Still other forms of headwear include decorative or fashion headwear such as illustrated in FIG. 39, where a hairband has been fitted with bilaterally position stimulation elements 104. In a similar manner, hairclips, barrettes, tiaras and other head worn fashion accessories may have the stimulation elements 104 incorporated therein to provide a therapeutic benefit. Further, hairbands (FIG. 40), sweat bands, bandannas and other head-worn fabrics may have stimulation elements incorporated therein for the benefit of the individual wearing the article.

Jewelry Embodiments

Figure 41:
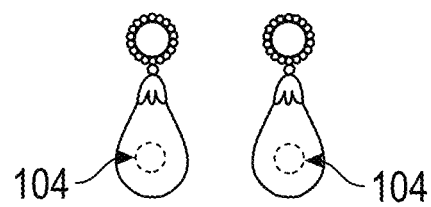
FIGS. 41-42 are illustrations of jewelry embodiments incorporating bilateral stimulation elements in accordance with a non-limiting embodiment.
Figure 42:
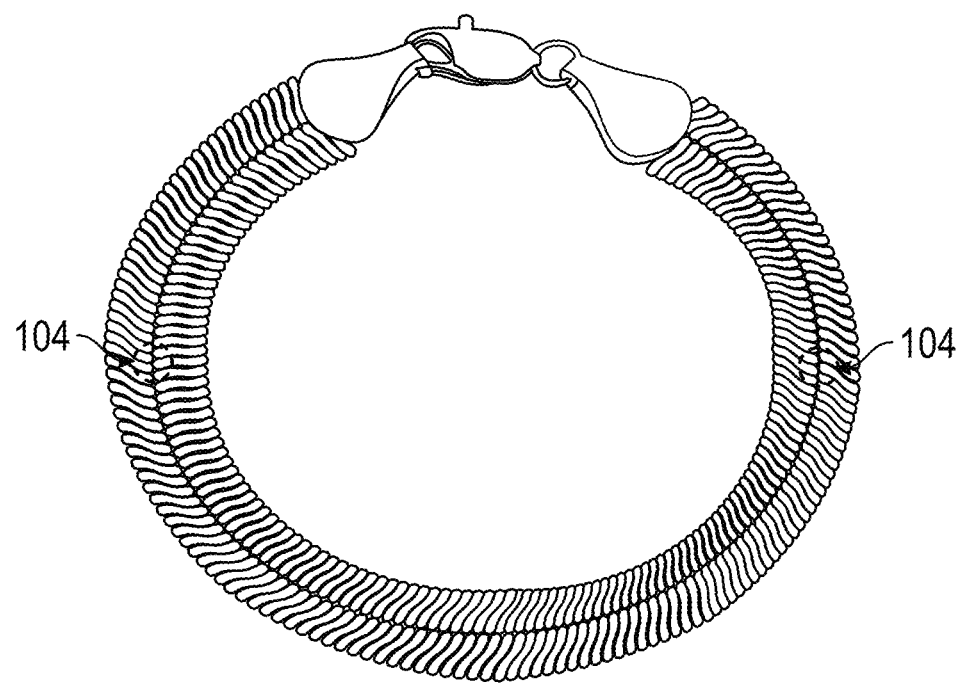

As previously discussed in connection with FIG. 19, the present disclosure contemplates that the stimulation elements 104 could be implemented in a wristwatch or other form of wrist-worn jewelry. Similarly, the stimulation elements 104 could be incorporated into earrings as illustrated in FIG. 41. As will be appreciated, earrings naturally bilaterally position the stimulation elements on either side the head and can provide a therapeutic benefit when activated by the mobile device as discussed above. Additionally, necklaces can be used bilaterally position the stimulation elements 104 on individual as illustrated in FIG. 42.

Furniture Embodiments

Figure 43:
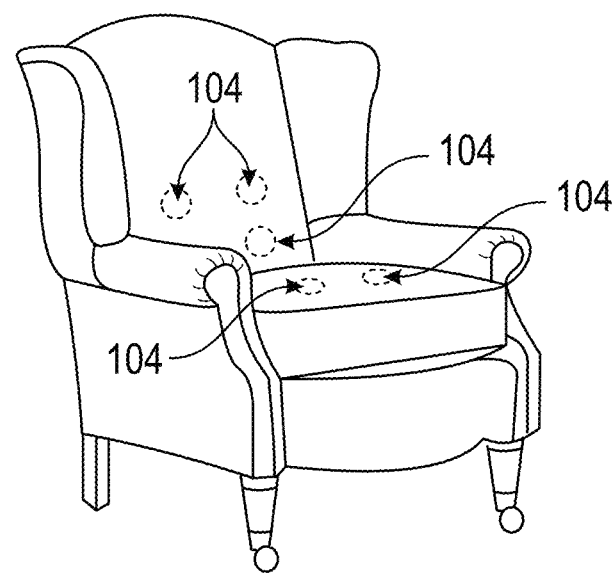
FIGS. 43-48 are illustrations of furniture embodiments incorporating bilateral stimulation elements in accordance with a non-limiting embodiment.
Figure 44:
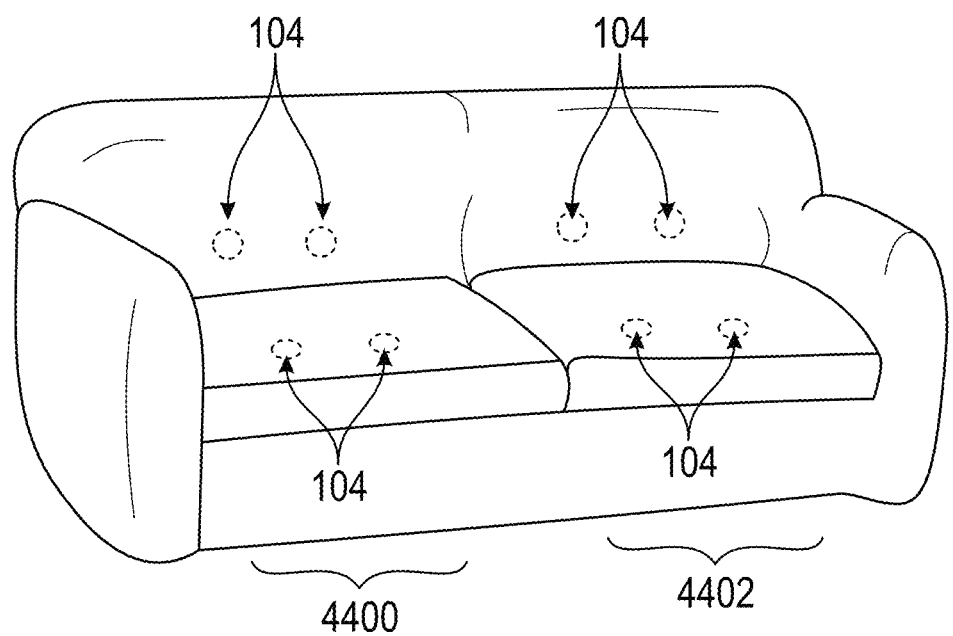
Figure 45:
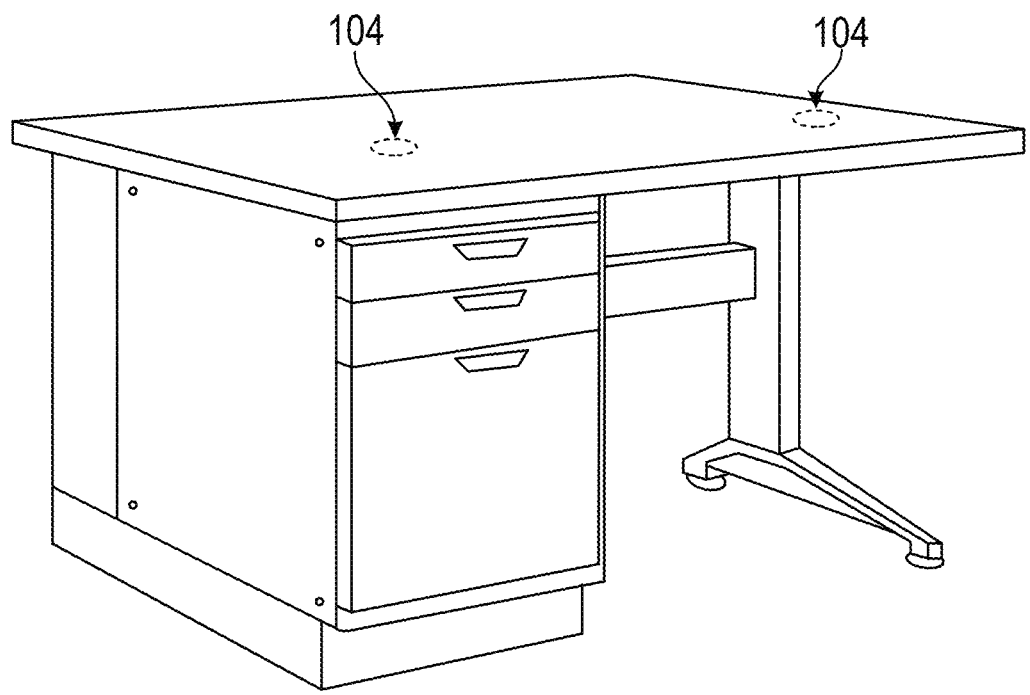
Figure 46:
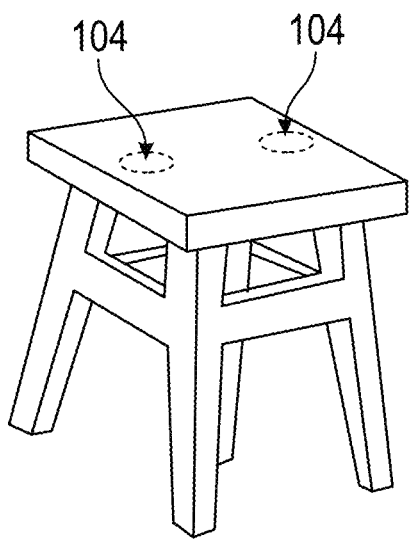
Figure 47:
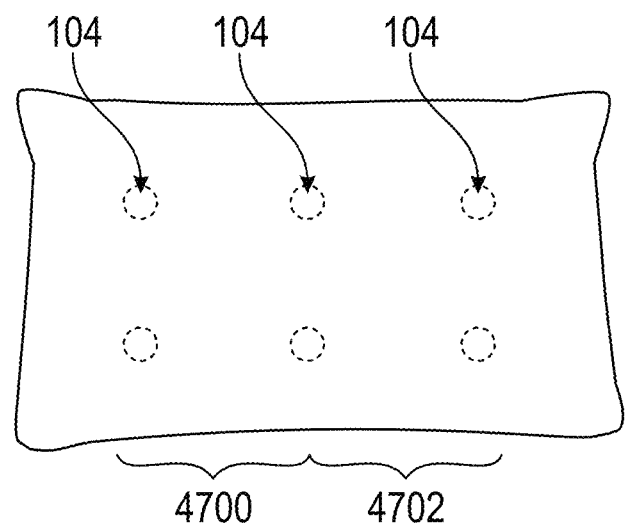
Figure 48:
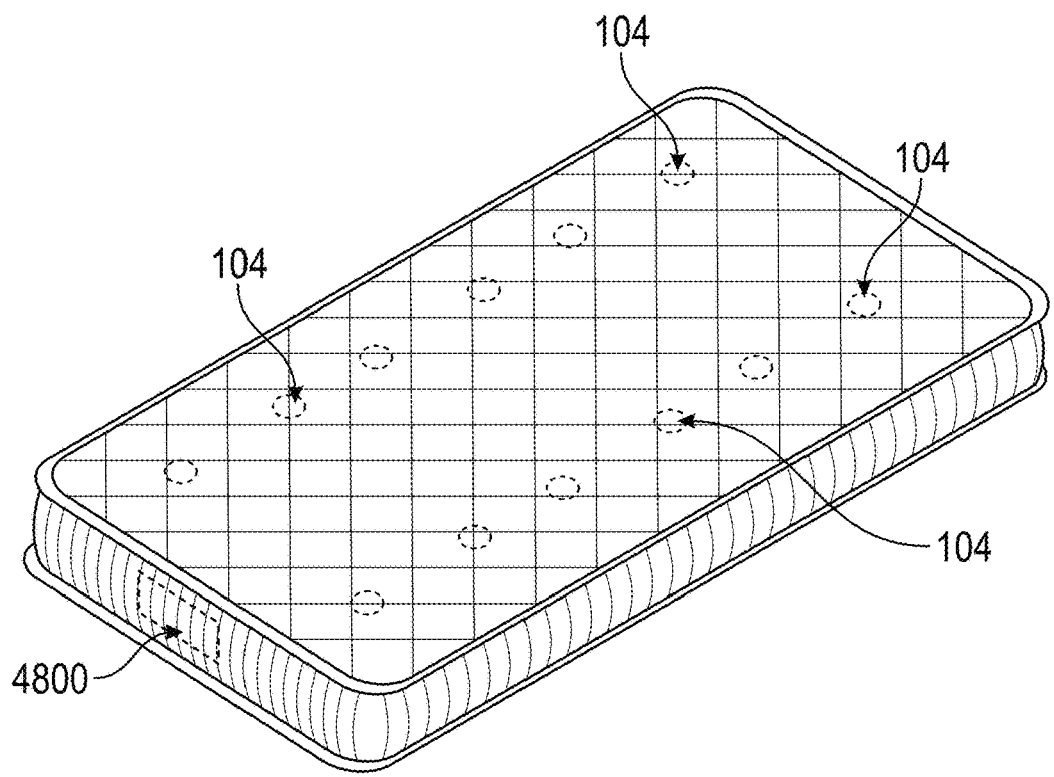

Furniture provides a natural platform into which the stimulation elements can be incorporated for the therapeutic benefit of individuals using the furniture. Generally, an individual sitting or reclining on a piece of furniture is par-stationary meaning that the individual is not mobile but may move or reposition him/herself on the furniture so as not to be considered fully stationary. FIG. 43 illustrates a chair having various stimulation elements 104 incorporated into the seat, lumbar area and back of the chair. The chair can be a kitchen chair, desk chair reclining chair or a so-called "easy chair" as illustrated in FIG. 43. In furniture embodiments, it may be advantageous to employ stimulation elements arranged in arrays as discussed in connection with FIG. 14 above. Moreover, the stimulation elements may incorporate the pressure sensor 212 as discussed above in connection with FIG. 15. Sofas are another article of furniture into which the stimulation elements 104 can be incorporated. Since multiple individuals may sit in a sofa the present disclosure contemplates that one individual may activate one array 4400 via his mobile device and another individual may activate another stimulation element array 4402 by her mobile device. This configuration may be useful in sectional sofas, loveseats or other multi-person furniture. Desks and tables are another article of furniture into which the stimulation elements 104 can be incorporated. As illustrated in FIG. 45 stimulation elements may be built into the desktop so that the individual seated at the desk can place her/his hands over the stimulation element to receive the therapeutic benefit at any time during the day or evening. Children in pediatric embodiments are also contemplated by the present disclosure. As illustrated in FIG. 46, stimulation elements 104 can be incorporated into a child's stool which can benefit the child by reducing stress and increasing concentration to keep the child on-task during an activity. Additionally, the stool could be used to reduce stress and anxiety during a minor disciplinary action such as a "timeout". Pillows and mattresses also provide an excellent platform for incorporating the stimulation elements 104 for evening relaxation. As illustrated in FIG. 47, stimulation elements can be built into a pillow or can be built into a pillow cover into which the pillow is inserted. Depending on the individuals sleep position, the mobile device can activate stimulation array 4700 or 4702 depending upon the pressure sensor readings provided by the pressure sensor 212 (see FIG. 15) to provide bilateral stimulation to the individuals head. FIG. 48 illustrates a mattress having an array of sensors positioned along either side of the mattress. One or more sensors in the bilateral array can be activated depending upon the pressure sensor readings provided by the pressure sensor 212 so that those vibrating elements 104 that are not in therapeutic contact with the individual do not vibrate and waste energy. In embodiments such as the mattress of FIG. 48 that employ several stimulation elements, it may be advantageous to have a removable battery 4800 that can be recharged and reconnected to the bilateral array as opposed to individually recharging each stimulator 104.

Mobility Embodiments

Figure 49:
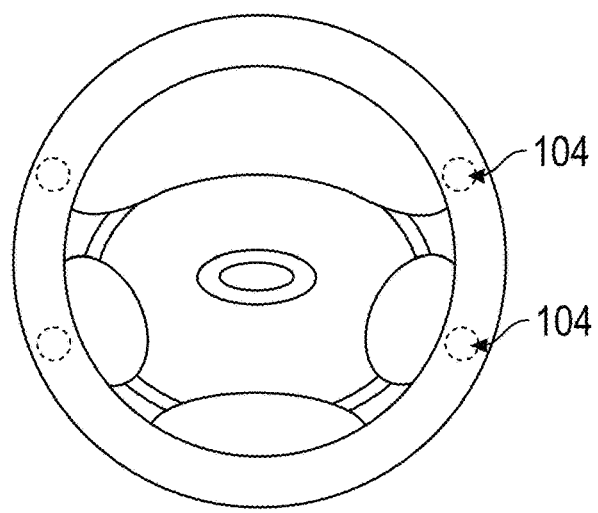
FIGS. 49-56 are illustrations of mobility embodiments incorporating bilateral stimulation elements in accordance with a non-limiting embodiment.
Figure 50:
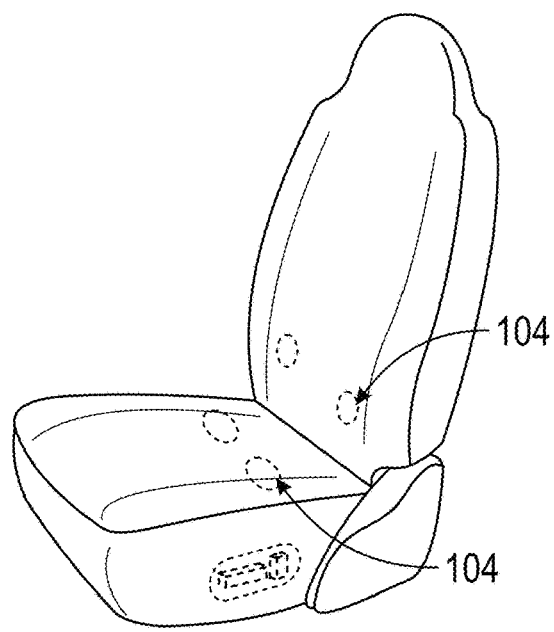
Figure 51:
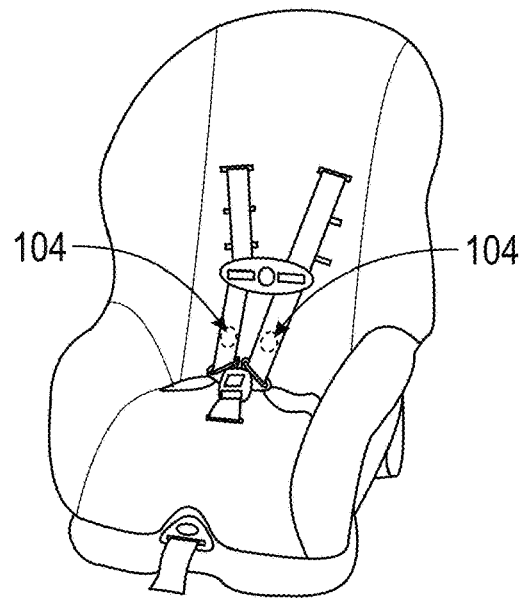
Figure 52:
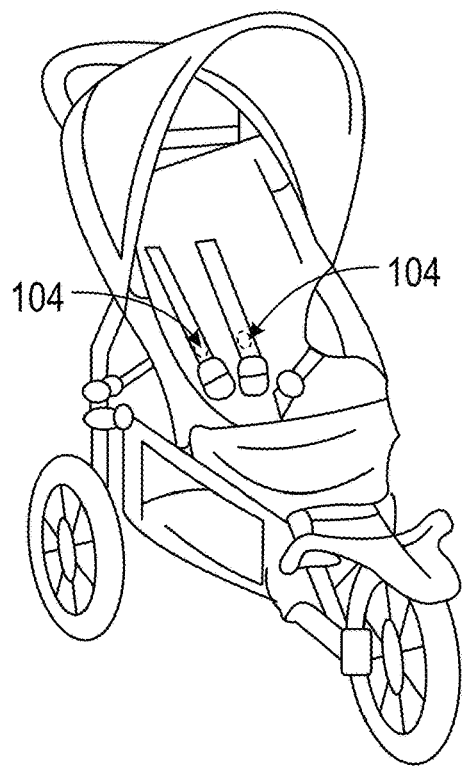
Figure 53:
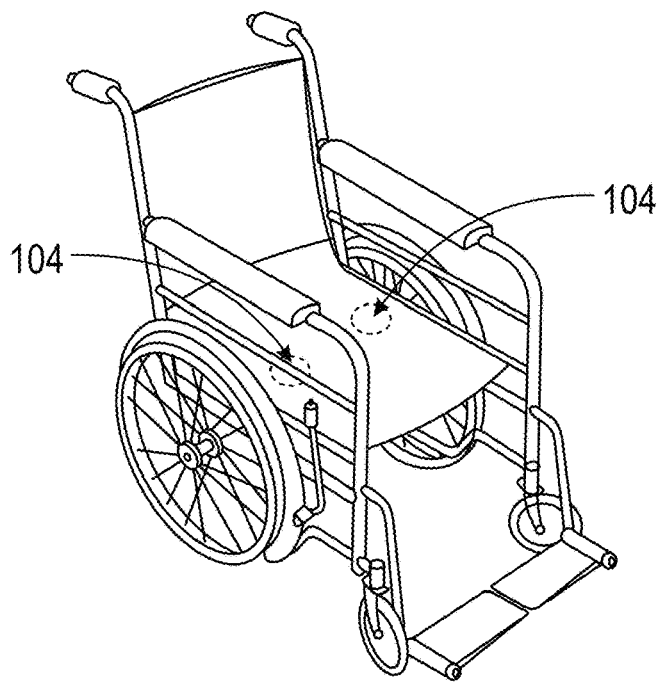
Figure 54:
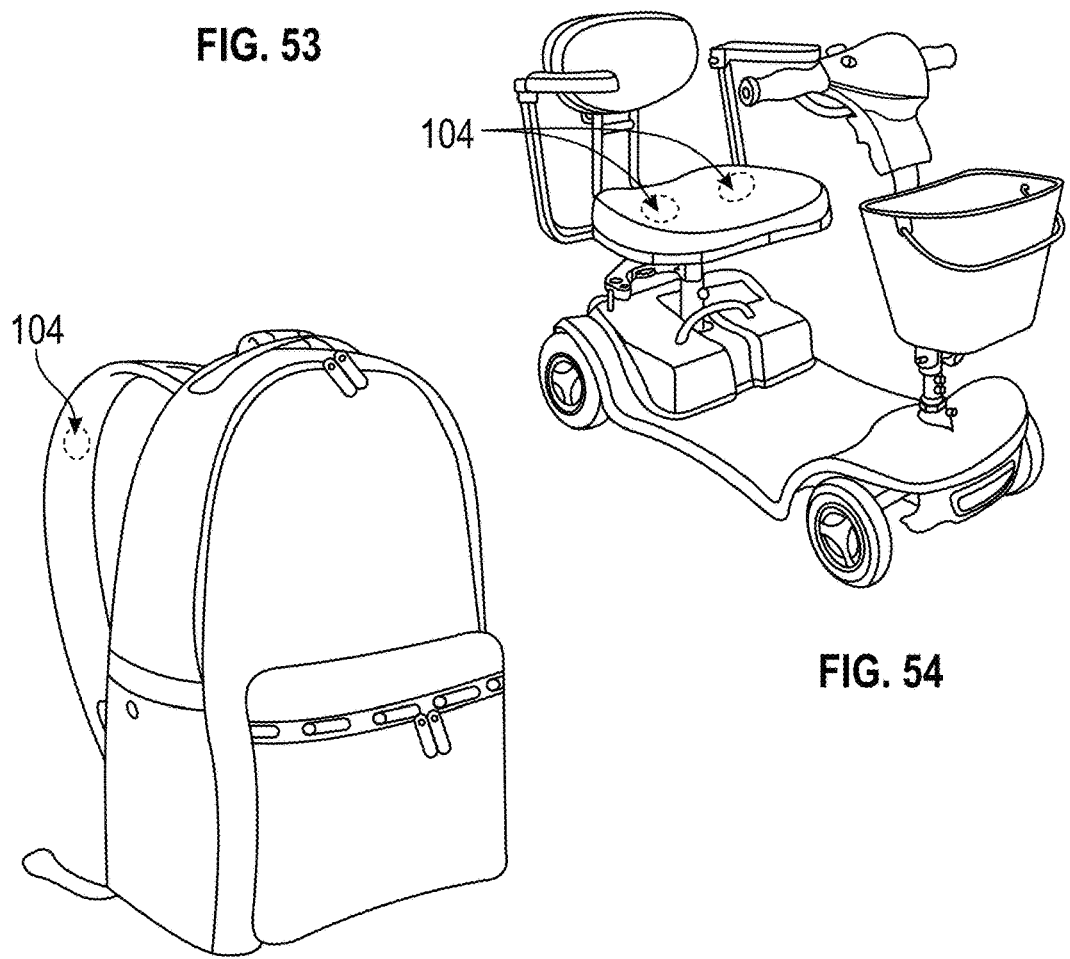
Figure 55:
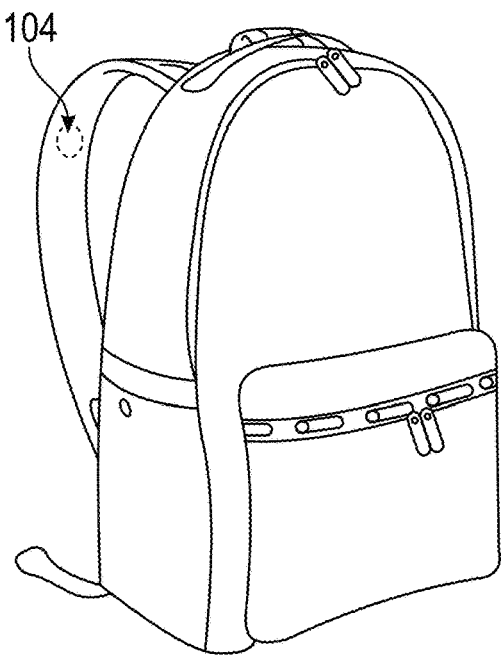
Figure 56:
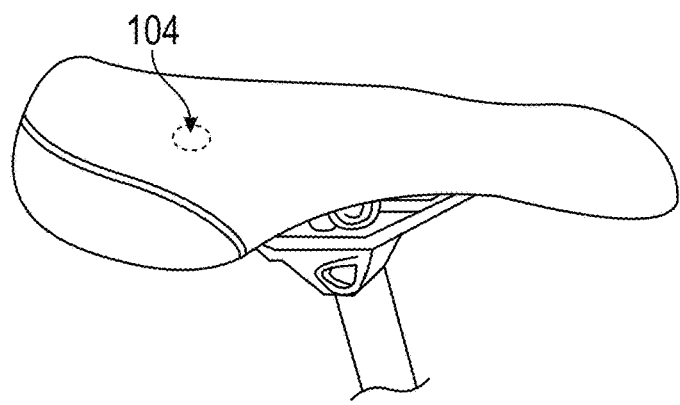

FIGS. 49-56 illustrate articles of daily life that promote mobility for an individual. The present disclosure contemplates that the stimulation elements 104 can be incorporated into a wide variety of articles promoting or supporting mobility of individual so as to be able to provide the therapeutic benefit at any time. For example, FIG. 49 illustrates stimulation elements 104 incorporated into the steering wheel the vehicle. Additionally, the stimulation elements 104 could be built into the vehicle seat as illustrated in FIG. 50 in a similar manner as described above for chairs in connection with FIG. 43. Moreover, vehicle passengers can benefit by having the stimulation elements 104 built into passenger seats including car seats for infants as illustrated in FIG. 51. In this way, an unhappy or crying infant may be relaxed by the therapeutic benefit while riding in a vehicle. Another common article supporting mobility for children is a stroller as illustrated in FIG. 52. Stimulation elements 104 can be built into the seat of the stroller and activated by the mobile device of the parent or caregiver pushing the stroller. Convalescent and elderly individuals may benefit by having the stimulation elements 104 built on to wheelchairs (FIG. 53) or powered scooters as illustrated in FIG. 54.

Toys & Game Embodiments.

Figure 57:
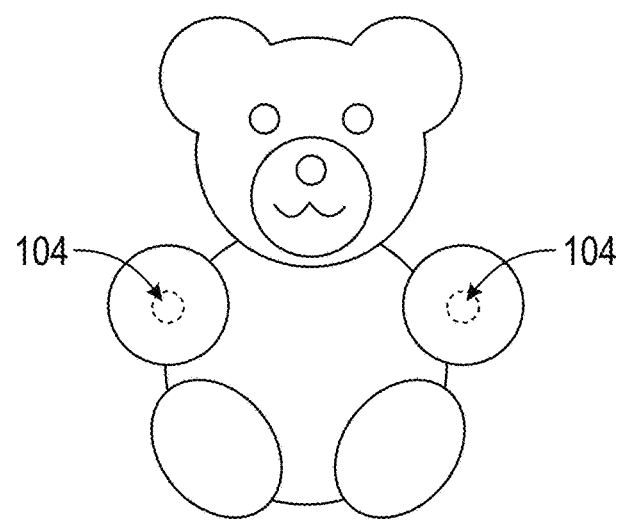
FIGS. 57-59 are illustrations of children toy embodiments incorporating bilateral stimulation elements in accordance with a non-limiting embodiment.
Figure 58:
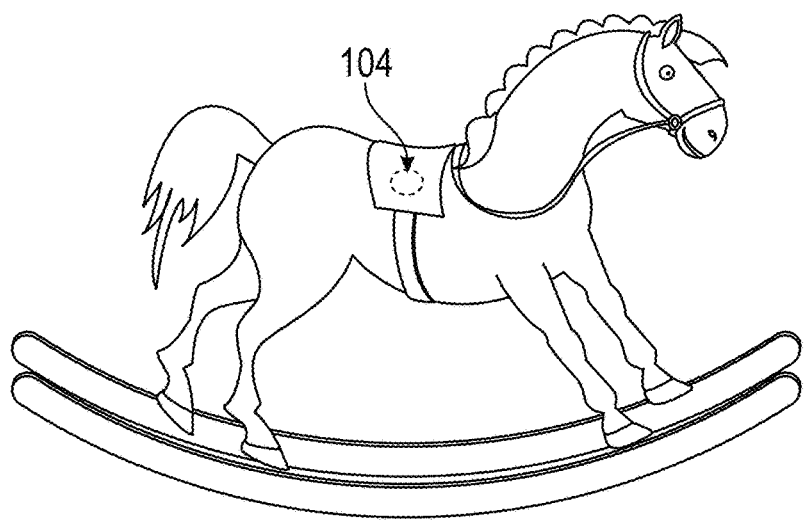
Figure 59:
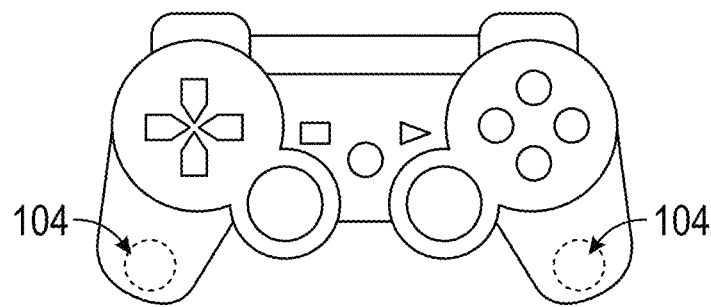

Children's toys and games provide another platform by which the therapeutic benefit can be delivered to children in a fun or entertaining way. For example, the stimulation elements 104 can be built into plush toys (e.g., a teddy bear) as illustrated in FIG. 57. In this way, a child can "hold hands" with the plush toy or hug the plush toy in a way as to bring the stimulation elements 104 into bilateral contact with the child. Rideable toys for children provide another platform by which stimulation elements 104 can be built into the riding area (e.g. seat or saddle) of a rocking horse (FIG. 58) or other ridable toy. For older children, stimulation elements 104 can be built into game controllers as illustrated in FIG. 59. In this manner, stress can be reduced, concentration enhanced and performance improved in a manner similar to that discussed above in connection with virtual reality games as illustrated in FIG. 37.

Figure 60:
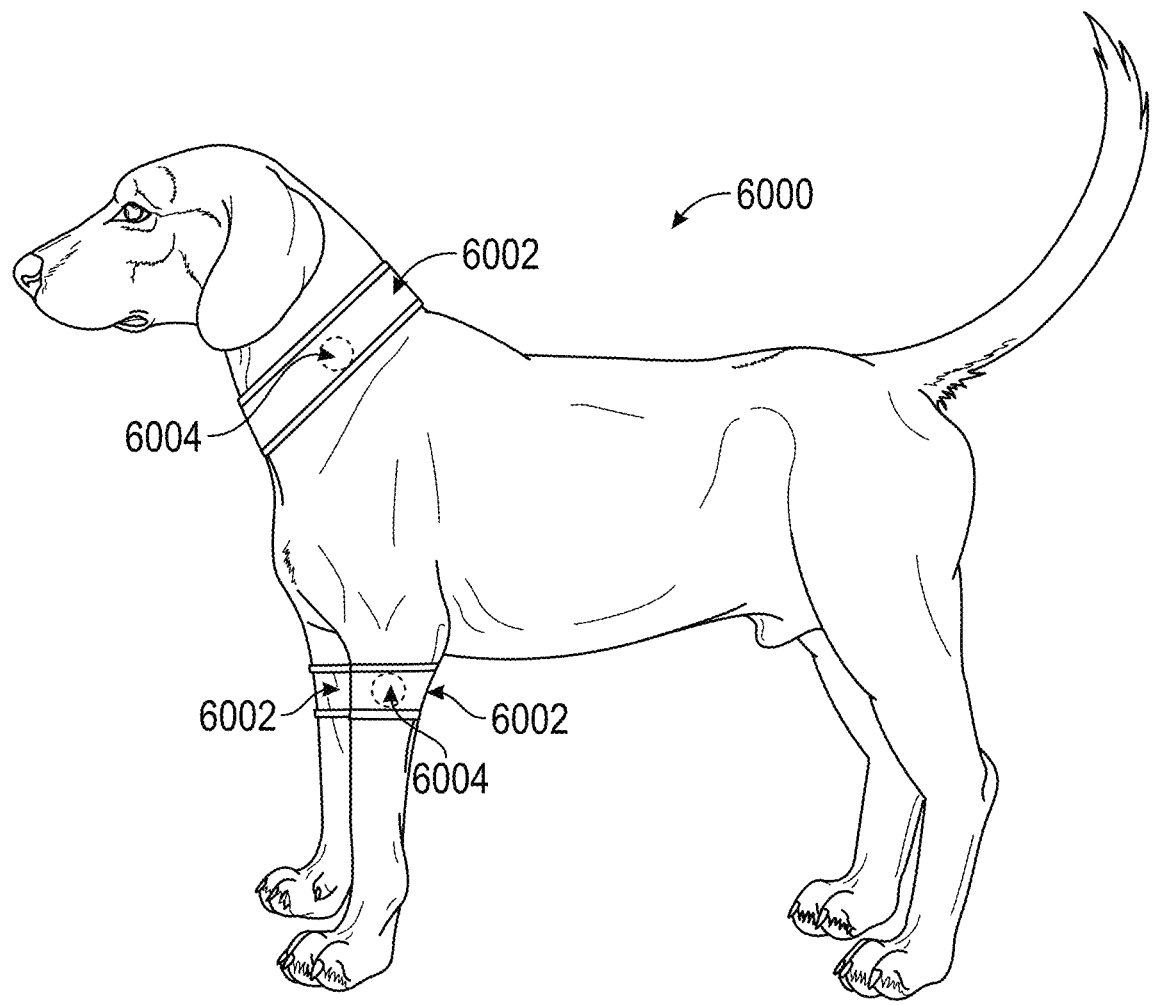
FIG. 60 is an illustration of an veterinary person showing exemplary positions for the stimulation elements in accordance with non-limiting embodiments.

Additionally, the benefits afforded by the present disclosure are not limited to human persons. Veterinary persons can also benefit as show in FIG. 60. As illustrated in this non-limiting example, a veterinary person 6000 (a dog in this example) has a band 6002 (similar to that discussed in connection with FIG. 60 having bi-laterally placed (one shown in FIG. 60) vibrating stimulation elements 6004 (similar to vibrating elements 104). A collar example and front leg example are illustrated in FIG. 60. Those skilled in the art will appreciate that other placement locations are possible. The benefits of the present disclosure can be seen not only via the animal's improved demeanor and attention, but objectively as well via an EEG or other tests.

While the present disclosure has been described in terms of improving performance or quality of life by reduction in stress, it will be appreciated by those skilled in the art that the therapeutic benefits offered by the present disclosure may also offer the possibility of aiding in the treatment of: attention deficit disorder, obsessive/compulsive disorder, clinical depression, panic disorder, anxiety, eating disorder, sleep disorder and learning disabilities. The stress relieving benefits of the present disclosure can assist person in real or imagined situations in everyday live, relieve stress or anxiety prior to surgery or a medical procedure (or themselves or a family member), relieve post-surgical and physical therapy stress during recovery.

The disclosed methods and systems provide asynchronous (or continuous) alternating bilateral stimulation to support the reduction of stress in individuals. It will be appreciated that the disclosed asynchronous methods and systems provide an advantage with the overlapping time period of simultaneous stimulation which enhances the bi-lateral impact in the somatosensory areas of the person's brain. It will also be appreciated that the disclosed continuous methods and systems provide an advantage by not allowing time for the person's brain to activate the somatosensory areas of the individual's brain. The disclosed asynchronous and continuous bi-lateral stimulations regimes provides an advantage over conventional bi-lateral stimulators in ensuring that the stimulation gap commonly used in conventional bi-lateral stimulators will not allow the brain to activate the sympathetic system.

It will be appreciated that the various illustrative logical blocks/tasks/steps, modules, circuits, and method steps described in connection with the embodiments disclosed herein may be implemented as electronic hardware, computer software, or combinations of both. Some of the embodiments and implementations are described above in terms of functional and/or logical block components or modules and various processing steps. However, it should be appreciated that such block components or modules may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope as set forth in the claims.

For example, an embodiment of a system or a component may employ various integrated circuit components, for example, memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The word exemplary is used exclusively herein to mean serving as an example, instance, or illustration. Any embodiment described herein as "exemplary" is not necessarily to be construed as preferred or advantageous over other embodiments.

The steps of a method described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as first, second, third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as connect or coupled to that are used in describing a relationship between different elements does not imply that a direct physical connection must be made between these elements. For example, two elements may be connected to each other physically, electronically, logically, or in any other manner, through one or more additional elements.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing the exemplary embodiment or exemplary embodiments.

What is claimed is:

1. A method for providing a therapeutic benefit to a person wearing a first wrist-worn article and a second wrist-worn article having, respectively, a first tactile stimulator and second tactile stimulator, the first and second wrist-worn articles being separately bilaterally positioned on each wrist to be in therapeutic contact with the person when the first and second wrist-worn articles are worn by the person, comprising:
   receiving, at a mobile device, an input selecting an intensity selection for bilateral stimulation;
   receiving, at the mobile device, an input selecting a duration selection for the bilateral stimulation;
   receiving, at the mobile device, an operating condition input comprising selecting an overlap selection for the bilateral stimulation, wherein the operation of the first and second tactile stimulators provides only for uninterrupted stimulation with or without an overlap, and wherein the overlap selection defines a degree of asynchronous stimulation the person receives from the first tactile stimulator and second tactile stimulator;
   activating, via a wireless controller in the mobile device, the first tactile stimulator to provide a first stimulation for a first time period corresponding to the duration selection;
   activating, via the controller, the second tactile stimulator to apply a second stimulation for a second time period corresponding to the duration selection beginning either prior to or simultaneously with the cessation of the first time period responsive to the overlap selection, wherein a change in the overlap selection from an initial overlap selection state to a changed overlap selection state causes a measurable change in the amount of overlap in the first stimulation and the second stimulation in at least a next iteration of the first and second stimulations according to the selection and the change in the amount of overlap occurs without a graduated transition;
   whereby, the first and second stimulations are applied bilaterally to the body of the person via the wrist-worn articles to provide bilateral uninterrupted stimulation, comprising, if selected, asynchronous stimulation with an overlapping stimulation period between the first stimulation and second stimulation to provide the therapeutic benefit to the person, and wherein tactile stimulation is the only mechanical stimulation of the person caused by the operation of the first and second stimulators under control of the wireless controller.

2. The method of claim 1, wherein the first stimulation and second stimulation are substantially uniform in speed and intensity during the first time period and the second time period, respectively.

3. The method of claim 1, wherein the first stimulation and second stimulation are substantially uniform in speed and increase in intensity during the first time period and the second time period, respectively.

4. The method of claim 1, wherein the first stimulation and second stimulation are substantially uniform in intensity and increase in speed during the first time period and the second time period, respectively.

5. The method of claim 1, wherein the first stimulation and second stimulation increase in intensity and speed during the first time period and the second time period, respectively.

6. The method of claim 1, wherein the first stimulation and second stimulation are substantially uniform in intensity and decrease in speed during the first time period and the second time period, respectively.

7. The method of claim 1, wherein the first stimulation and second stimulation are substantially uniform in speed and decrease in intensity during the first time period and the second time period, respectively.

8. The method of claim 1, wherein the first stimulation and second stimulation decrease in intensity and speed during the first time period and the second time period, respectively.

9. The method of claim 1, wherein the first stimulation and the second stimulation are vibratory stimulations.

10. The method of claim 1, wherein the length of each period of stimulation during which there is no overlap in at least some overlap setting sections is at least at least two times the length of one or more period(s) of stimulation during which there is overlap.

11. A method for providing a therapeutic benefit to a person wearing a pair of footwear, a first footwear of the pair of footwear having a first tactile stimulator positioned therein such that the first tactile stimulator will be in therapeutic contact with the person when the first footwear is worn by the person, and a second footwear of the pair of footwear having a second tactile stimulator positioned therein such that the second tactile stimulator will be in therapeutic contact and separately bilaterally positioned on the person relative to the first tactile stimulator when the pair of footwear is worn by the person, comprising:
  receiving, at a mobile device, an input selecting an intensity selection for bilateral stimulation;
  receiving, at the mobile device, an input selecting a duration selection for the bilateral stimulation;
  receiving, at the mobile device, an operating condition input comprising selecting an overlap selection for the bilateral stimulation, wherein the operation of the first and second tactile stimulators provides only for uninterrupted stimulation with or without an overlap, and wherein the overlap selection defines a degree of asynchronous stimulation the person receives from the first tactile stimulator and second tactile stimulator;
  activating, via a wireless controller in the mobile device, the first tactile stimulator to provide a first stimulation for a first time period corresponding to the duration selection;
  activating, via the controller, the second tactile stimulator to apply a second stimulation for a second time period corresponding to the duration selection beginning either prior to or simultaneously with the cessation of the first time period responsive to the overlap selection, wherein a change in the overlap selection from an initial overlap selection state to a changed overlap selection state causes a measurable change in the amount of overlap in the first stimulation and the second stimulation in at least a next iteration of the first and second stimulations according to the selection and the change in the amount of overlap occurs without a graduated transition;
  whereby, the first and second stimulations are applied bilaterally to the body of the person via the pair of footwear to provide bilateral uninterrupted stimulation, comprising, if selected, asynchronous stimulation with an overlapping stimulation period between the first stimulation and second stimulation to provide the therapeutic benefit to the person, and wherein tactile stimulation is the only mechanical stimulation of the person caused by the operation of the first and second stimulators under control of the wireless controller.

12. The method of claim 11, wherein the first stimulation and second stimulation are substantially uniform in speed and intensity during the first time period and the second time period, respectively.

13. The method of claim 11, wherein the first stimulation and second stimulation are substantially uniform in speed and increase in intensity during the first time period and the second time period, respectively.

14. The method of claim 11, wherein the first stimulation and second stimulation are substantially uniform in intensity and increase in speed during the first time period and the second time period, respectively.

15. The method of claim 11, wherein the first stimulation and second stimulation increase in intensity and speed during the first time period and the second time period, respectively.

16. The method of claim 11, wherein the first stimulation and second stimulation are substantially uniform in intensity and decrease in speed during the first time period and the second time period, respectively.

17. The method of claim 11, wherein the first stimulation and second stimulation are substantially uniform in speed and decrease in intensity during the first time period and the second time period, respectively.

18. The method of claim 11, wherein the first stimulation and second stimulation decrease in intensity and speed during the first time period and the second time period, respectively.

19. The method of claim 11, wherein the first stimulation and the second stimulation are vibratory stimulations.

20. The method of claim 11, wherein the length of each period of stimulation during which there is no overlap in at least some overlap setting sections is at least at least two times the length of one or more period(s) of stimulation during which there is overlap.

21. The method of claim 11, wherein the first stimulation and second stimulation are substantially uniform in speed and decrease in intensity during the first time period and the second time period, respectively.

22. A method for providing a therapeutic benefit to a person wearing one or more articles of clothing worn on the wrist, arm, chest, leg, ankle, or waist, having a first tactile stimulator and a second tactile stimulator positioned therein to be bilaterally positioned in therapeutic contact with the person when the person is wearing the article of clothing, comprising:

receiving, at a mobile device, an input selecting an intensity selection for the bilateral stimulation;

receiving, at the mobile device, an input selecting a duration selection for the bilateral stimulation;

receiving, at the mobile device, an operation condition input comprising selecting an overlap selection for the bilateral stimulation, wherein the operation of the first and second tactile stimulators provides only for uninterrupted stimulation with or without an overlap, and wherein the overlap selection defines a degree of asynchronous stimulation the person receives from the first tactile stimulator and second tactile stimulator;

activating, via a wireless controller in the mobile device, the first tactile stimulator to provide a first stimulation for a first time period corresponding to the duration selection;

activating, via the controller, the second tactile stimulator to apply a second stimulation for a second time period corresponding to the duration selection beginning either prior to or simultaneously with the cessation of the first time period responsive to the overlap selection, wherein a change in the overlap selection from an initial overlap selection state to a changed overlap selection state causes a measurable change in the amount of overlap in the first stimulation and the second stimulation in at least a next iteration of the first and second stimulations according to the selection and the change in the amount of overlap occurs without a graduated transition;

whereby, the first and second stimulations are applied bilaterally to the body of the person via the article of clothing to provide bilateral, uninterrupted stimulation, comprising, if selected, asynchronous stimulation with an overlapping stimulation period between the first stimulation and second stimulation to provide the therapeutic benefit to the person, and wherein tactile stimulation is the only mechanical stimulation of the person caused by the operation of the first and second stimulators under control of the wireless controller.

23. The method of claim 22, wherein the first stimulation and the second stimulation are vibratory stimulations.

24. The method of claim 22, wherein the length of each period of stimulation during which there is no overlap in at least some overlap setting sections is at least at least two times the length of one or more period(s) of stimulation during which there is overlap.

25. The method of claim 22, wherein the first stimulation and second stimulation are substantially uniform in speed and decrease in intensity during the first time period and the second time period, respectively.

* * * * *